(12) United States Patent
Hoon

(10) Patent No.: US 8,039,218 B2
(45) Date of Patent: *Oct. 18, 2011

(54) DETECTION OF CANCER CELLS IN BODY FLUIDS

(75) Inventor: Dave S. B. Hoon, Los Angeles, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/227,575

(22) Filed: Sep. 14, 2005

(65) Prior Publication Data

US 2006/0115832 A1    Jun. 1, 2006

Related U.S. Application Data

(63) Continuation-in-part of application No. 10/713,808, filed on Nov. 14, 2003, now Pat. No. 7,910,295.

(60) Provisional application No. 60/426,216, filed on Nov. 14, 2002, provisional application No. 60/609,634, filed on Sep. 14, 2004.

(51) Int. Cl.
*G01N 33/53* (2006.01)

(52) U.S. Cl. ......................................................... 435/7.1

(58) Field of Classification Search ........................ None
See application file for complete search history.

(56) References Cited

U.S. PATENT DOCUMENTS

| 6,057,105 | A | * | 5/2000 | Hoon et al. ...................... 435/6 |
| 6,248,535 | B1 | | 6/2001 | Danenberg et al. |
| 6,331,393 | B1 | | 12/2001 | Laird et al. |
| 6,428,963 | B2 | | 8/2002 | Danenberg et al. |
| 6,518,416 | B1 | | 2/2003 | Danenberg |
| 6,573,052 | B2 | | 6/2003 | Danenberg |
| 6,602,670 | B2 | | 8/2003 | Danenberg |
| 6,610,488 | B2 | | 8/2003 | Danenberg et al. |
| 6,613,518 | B2 | | 9/2003 | Danenberg |

FOREIGN PATENT DOCUMENTS

| EP | 0 520 794 A1 | 12/1992 |
| WO | 96/29430 | 9/1996 |
| WO | 99/10528 | 3/1999 |
| WO | 02/070571 | 9/2002 |
| WO | 02/070751 A1 | 9/2002 |
| WO | 2004/045521 A | 6/2004 |

OTHER PUBLICATIONS

Tockman et al (Cancer Res., 1992, 52:2711s-2718s).*
Scholl et al (Feb. 2001, Cancer Research, 61:823-826).*
Johansson et al (2000, Clinical Chemistry, 46(7): 921-927).*
Hoon et al (US Patent 6,057,105; May 2, 2000).*
Scholl et al (Feb. 2001, Cancer Research, 61:823-826) and.*
Scoggins et al (Journal of Clinical Oncology, 2006, 24(18): 2849-2857).*
Mocellin et al (TRENDS in Molecular Medicine, 2003, 9(5):189-195).*
Tsao et al (Arch Dermatol, 2001, 137:325-330).*
Gerber et al (Journal of Clinical Oncology, 2001, 19(4): 960-971).*
Hilari et al (Ann Surg Oncol, 2009, 16(1): 177-185).*
Tatilidil et al (Modern Pathology, 2007, 20: 427-434).*
Denninghoff et al (Mol Diag, 2004, 8(4): Abstract).*
Hoon et al (J Clin Oncol, 1995, 13(18): 2109-2116).*
Bilchek et al., "Molecular Detection of Metastatic Pancreatic Carcinoma Cells Using a Multimarker Reverse Transcriptase-Polymerase Chain Reaction Assay". Cancer. 88:1037-1044 (2000).
Balch et al., "Efficacy of an Elective Regional Lymph Node Dissection of 1 to 4 mm Thick Melanomas for Patients 60 Years of Age and Younger," Ann. Surg. 1996; 224:255-63.
Balch et al., A Comparison of Prognostic Factors and Surgical Results in 1,786 Patients with Localized (stage I) Melanoma Treated in Alabama, USA and New South Wales, Australia, Ann. Surg. 196:677-684, 1982.
Bilchik, A.J., et al., "Molecular Staging of Early Colon Cancer on the Basis of Sentinel Node Analysis: a Multicenter Phase I Trial," J. Clin. Oncol., 19: 1128-1136, 2001.
Bostick, P.J. et al., "Prognostic Significance of Occult Metastases Detected by Sentinel Lymphadenectomy and Reverse Transcriptase-Polymerase Chain Reaction in Early-Stage Melanoma Patients," J. Clin. Oncol., 17:3238-3244, 1999.
Cascinelli et al., "Immediate or Delayed Dissection of Regional Nodes in Patients with Melanoma of the Trunk: a Randomized Trial," WHO Melanoma Programme. Lancet, 1998; 351:796-6.
Clegg, R.M., "Fluorescence Energy Transfer.," Curr. Opin. Biotech, 6: 103-110, 1995.
Cochran et al., "Occult Melanoma in Lymph Nodes Detected by Antiserum to S-100 Protein," Int. J. Cancer, 1984; 34:159-63.
Final Version of the American Joint Committee on Cancer Staging System for Cutaneous Melanoma, J. Clin. Oncol., 16: 3635-3648, 2001.
Hatta et al. (Melanoma Research, Aug. 1999, 9(4): abstract).
Henderson, A.R., "Assessing Test Accuracy and Its Clinical Consequences: a Primer for Receiver Operating Characteristic Curve Analysis," Ann Clin Biochem 1993; 30:521-29.
Hoon, D.S. et al., "Modulation of Human Melanoma Cells by Interleukin-4 and in Combination with gamma-Interferon or alpha-Tumor Necrosis Factor," Cancer Res. 1991; 51: 2002-8.
Jemal et al., Cancer Statistics 2002, CA Cancer J. Clin., 52: 23-47, 2002.
Kawakami et al., "Identification of a Human Melanoma Antigen Recognized by Tumor-Infiltrating Lymphocytes Associated with In Vivo Tumor Rejection," Proc. Natl. Acad. Sci., USA, 91: 6458-6462, 1994.

(Continued)

*Primary Examiner* — Sean Aeder
(74) *Attorney, Agent, or Firm* — Brooks Kushman P.C.

(57) ABSTRACT

A method of detecting circulating melanoma or carcinoma cells in a subject. The method comprises obtaining a body fluid from a subject and detecting the expression of a panel of genes in the body fluid, wherein the expression of the panel of genes indicates the presence of circulating melanoma or carcinoma cells in the subject. Genes useful for detecting melanoma cells includes GalNAc-T, MAGE-A3, MART-1, PAX-3, and TRP-2; genes useful for detecting carcinoma cells include C-Met, MAGE-A3, Stanniocalcin-1, Stanniocalcin-2, mammaglobin, HSP27, GalNAc-T, CK20, and β-HCG. Also disclosed are kits containing agents for detecting the expression of these genes.

10 Claims, 5 Drawing Sheets

OTHER PUBLICATIONS

Keilholtz, Ulrich et al., "Quantitative Detection of Circulating Tumor Cells in Cutaneous and Ocular Melanoma and Quality Assessment by Real-time Reverse Transcriptase-Polymerase Chain Reaction," Clinical Cancer Research, v. 10, Mar. 1, 2004, pp. 1605-1612.

Kocher et al., "Identification of Genes Differentially Expressed in Melanoma Sublines Derived from a Single Surgical Specimen Characterized by Different Sensitivity to Cytotoxic T-lymphocyte Activity," Dept. of Surgery, Z.L.F., pp. 617-624.

Koyanagi et al., "Serial Monitoring of Circulating Melanoma Cells During Neoadjuvant Biochemotherapy for Stage III Melanoma: Outcome Prediction in a Multicenter Trial," J. Clin. Oncol., 2005, 23(31):8057-8064.

Li et al., "Clinical Relevance of Molecular Staging for Melanoma: Comparison of RT-PCTR and Immunohistochemistry Staining in Sentinel Lymph Nodes of Patients with Melanoma," Ann Surg. 2000; 231:795-803.

Masuda, N. et al., "Analysis of Chemical Modification of RNA from Formalin-fix Samples and Optimization of Molecular Biology Applications for Such Samples," Nuc. Acid. Res. 19991; 27: 4436-43.

Mitas, M. et al., "Quantitative Real-time RT-PCR Detection of Breast Cancer Micrometastasis Using A Multigene Marker Panel," Int. J. Cancer 2001; 93: 162-71.

Morton, D.L. et al., "Technical Details of Intraoperative Lymphatic Mapping for Early Stage Melanoma," Arch. Surg. 127:392-399, 1992.

Morton, D.L. et al., "Intraoperative Lymphatic Mapping and Selective Cervical Lymphadenectomy for Early-Stage Melanomas of the Head and Neck," J. Clin. Oncol. 1993; 11:1751-6.

Morton, D.L. et al., "Vaccine Therapy for Malignant Melanoma," CA Cancer J. Clin. 1996; 46: 225-44.

Morton, D.L. et al., "Validation of the Accuracy of Intraoperative Lymphatic Mapping and Sentinel Lymphadenectomy for Early-Stage Melanoma: Multicenter Trial," Multicenter Selective Lymphadenectomy Trial Group, Ann Surg. 1999; 230:453-63.

Morton et al., "Prolongation of Survival in Metastatic Melanoma After Active Specific Immunotherapy with a New Polyvalent Melanoma Vaccine," Ann. Surg. 1992; 216:463-82.

O'Day, S.J. et al., "Maintenance Biotherapy for Metastatic Melanoma with Interleukin 2 and Granulocyte Macrophage-Colony Stimulating Factor Improves Survival for Patients Responding to Induction Concurrent Biochemotherapy," Clin. Cancer Res. 2002; 8: 2775-81.

Rigel et al., "The Incidence of Malignant Melanoma in the United States: Issues as we Approach the 21st Century," J. Am. Acad. Dermotol., 34: 839-847, 1996.

Sarantou, T. et al., "Melanoma-Associated Antigens as Messenger RNA Detection Markers for Melanoma," Recent Results Cancer Res. 2001; 158: 78-92.

Schuster, R. et al., "Quantitative Real-Time RT-PCR for Detection of Disseminated Tumor Cells in Peripheral Blood of Patients with Colorectal Cancer Using Different mRNA Markers," Ins. J. Cancer, v. 108, n. 2, pp. 219-227, Jan. 10, 2004.

Shirota, Y. et al., "ERCCI1 and Thymidylate Synthase mRNA Levels Predict Survival for Colorectal Cancer Patients Receiving Combination Oxaliplatin and Fluorouracil Chemotherapy," J. Clin. Oncol. 2001; 19: 4298-304.

Shivers et al., "Molecular Staging of Malignant Melanoma: Correlation with Clinical Outcome," JAMA 1998; 280:1410-5.

Sorensen, B.S. et al., "Quantification of Melanoma Cell-specific MART-I mRNA in Peripheral Blood by a Calibrated Competitive Reverse Transcription-PCR," Clinical Chemistry 46:12, Sep. 26, 2000, pp. 1923-1928.

Specht, K. et al., "Quantitative Gene Expression Anaylsis in Microdissected Archival Tissue by Real-Time RT-PCR," J. Mol. Med. 78: B27, 2000 (Abstract).

Taback, B. et al., "The Clinical Utility of Multimarker RT-PCR in the Detection of Occult Metastasis in Patients with Melanoma," Recent Results Cancer Res. 2001; 158:78-92.

Tai, T. et al., "Ganglioside GM2 as a Human Tumor Antigen (OFA-I-1)," Proc. Nat'l. Acad. Sci. US 1983; 80: 5392-6.

Vachtenheim et al., "Expression of Genes for Microphthalmia Isoforms, PAX3 and MSG1, in Humane Melanomas," Cellular and Molecular Biology, v. 45, pp. 1075-1082 (1999).

Balch et al., J. Clinical Oncology, 19:3635-48, 2001, "*Final Version of the American Joint Committee on Cancer Staging System for Cutaneous Melanoma*".

Balch et al., Semin. Surgical Oncology, 21:43-52, 2003, "*New TNM Melanoma Staging System: Linking Biology and Natural History to Clinical Outcomes*".

Bostick et al., J. Clinical Oncology, 16:2632-40, 1998, "*Limitations of Specific Reverse-Transcriptase Polymerase Chain Reaction Markers in the Detection of Metastases in the Lymph Nodes and Blood of Breast Cancer Patients*".

Bouras et al., Cancer Research 62:1289-95, 2002, "*Stanniocalcin 2 Is an Enstrogen-responsive Gene Coexpressed with the Estrogen Receptor in Human Breast Cancer*".

Bustin, Journal of Molecular Endocrinology 25:169-93, 2000, "*Absolute Quantification of mRNA Using Reel-Time Reverse Transcription Polymerase Chain Reaction Assays*".

Chang et al., Endocrine-Related Cancer, vol. 10:359-373, 2003, "*Mammalian Stanniocalcins and Cancer*".

Choi et al., Vet. Pathology, 40:713-718, 2003, "*Comparison of Tyrosinase-Related Protein-2, S-100, and Melan A Immunoreactivity in Canine Amelanotic Melanomas*".

Coulie et al., PNAS, vol. 98, pp. 10290-10295, 2001, "*A Monoclonal Cytolytic T-Lymphocyte Response Observed in a Melanoma Patient Vaccinated with a Tumor-Specific Antigenic Peptide Encoded by Gene MAGE-3*".

Cristofanilli et al., N. England J. Med. 351:781-91, 2004, "*Circulating Tumor Cells, Disease Progression, and Survival in Metastatic Breast Cancer*".

Gaugler et al., J. Exp. Med. 179:921-30, 1994, "*Human Gene MAGE-3 Codes for an Antigen Recognized on a Melanoma by Autologous Cytolytic T. Lymphocytes*".

Glaser et al., J. Clinical Oncology, 15:2818-25, 1997, "*Detection of Circulating Melanoma Cells by Specific Amplification of Tyrosinase Complementary DNA is not a Reliable Tumor Marker in Melanoma Patients: A Clinical Two-Center Study*".

Goding, Genes Dev. 14:1712-28, 2000, "*Mitf from Neural Crest to Melanoma: Signal Transduction and Transcription in the Melanocyte Lineage*".

Gradilone et al., Oncology Reports, vol. 10:217-222, 2003, "*Detection of CK19, CK20 and EGFR mRNAs In Peripheral Blood of Carcinoma Patients: Correlation with Clinical Stage of Disease*".

Hoon et al., J. Clinical Oncology, 13:2109-16, 1995, "*Detection of Occult Melanoma Cells in Blood with a Multiple-Marker Polymerase Chain Reaction Assay*".

Hoon et al., Cancer Research, 60:2253-7, 2000, "*Molecular Markers in Blood as Surrogate Prognostic Indicators of Melanoma Recurrence*".

Irie et al., Lancet 1:786-7, 1989, "*Human Monoclonal Antibody to Ganglioside GM2 for Melanoma Treatment*".

Jung et al., J. Clinical Oncology, 15:2826-31, 1997, "*Evaluation of Tyrosinase mRNA as a Tumor Marker in the Blood of Melanoma Patients*".

Kawakami et al., Proc. Natl. Acad. Scl. USA, 91:3515-9, 1994, "*Cloning of the Gene Coding for a Shared Human Melanoma Antigen Recognized by Autologous T Cells Infiltrating Into Tumor*".

Kawakami et al., J. Exp. Med. 180:347-52, 1994, "*Identification of the Immunodominant Peptides of the MART-1 Human Melanoma Antigen Recognized by the Majority of HLA-A2-Restriction Tumor Infiltrating Lymphocytes*".

Koyanagi et al., Clinical Chem. 51:981-8, 2005, "*Multimarker Quantitative Real-Time PCR Detection of Circulating Melanoma Cells in Peripheral Blood: Relation to Disease Stage in Melanoma Patients*".

Kuo et al., Clinical Cancer Research, vol. 4, 411-48, 1998, "*Assessment of Messenger RNA of β1-4-N-Acetylgatactosaminyltransferase as a Molecular Marker for Metastatic Melanoma*".

Marchetti et al., J. Pathology, vol. 195, 186-190, 2001, "*mRNA Markers of Breast Cancer Nodal Metastases: Comparison Between Mammaglobin and Carcinoembryonic Antigen in 248 Patients*".

Marincola et al., Adv. Immunol. 74:181-273, 2000, "*Escape of Human Solid Tumors from T-Cell Recognition: Molecular Mechanisms and Functional Significance*".

Miyashiro et al., Clinical Chem. 47:505-12, 2001, "*Molecular Strategy for Detecting Metastatic Cancers with Use of Multiple Tumor-Specific MAGE-A Genes*".

Palmieri et al., Journal of Clinical Oncology, vol. 19, No. 5, pp. 1437-1443, 2001, "*Detection of Occult Melanoma Cells in Paraffin-Embedded Histologically Negative Sentinel Lymph Nodes Using a Reverse Transcriptase Polymerase Chain Reaction Assay*".

Pantel et al., J. Natl. Cancer Inst. 91:1113-24, 1999, "*Detection and Clinical Importance of Micrometastatic Disease*".

Peng et al., J. Clinical Pathology, vol. 47, pp. 605-608, 1994, "*Multiple PCR Analyses on Trace Amounts of DNA Extracted from Fresh and Paraffin Wax Embedded Tissues After Random Hexamer Primer PCR Amplification*".

Sarantou et al., Cancer Research, 57:1371-6, 1997, "*Melanoma-Associated Antigens as Messenger RNA Detection Markers for Melanoma*".

Scholl et al., Cancer Research, 61:823-6, 2001, "*PAX3 is Expressed in Human Melanomas and Contributes to Tumor Cell Survival*".

Schultz et al., Cancer Research, 60:6272-5, 2000, "*A MAGE-A3 Peptide Presented by HLA-DP4 is Recognized on Tumor Cells by CD4+ Cytolytic T Lymphocytes*".

Soong et al., Clinical Cancer Research, vol. 7, 3423-3429, 2001, "*Quantitative Reverse Transcription-Polymerase Chain Reaction Detection of Cytokeratin 20 in Noncolorectal Lymph Nodes*".

Stathopoulou et al., Clinical Cancer Research, 9:5145-51, 2003, "*Real Time Quantification of CK-19 mRNA-Positive Cells In Peripheral Blood of Breast Cancer Patients Using the Lightcycler System*".

Taback et al., Cancer Research, 61, 8845-8850, 2001, "*Detection of Occult Metastatic Breast Cancer Cells in Blood by a Multimolecular Marker Assay; Correlation with Clinical Stage of Disease*".

Takeuchi et al., Cancer Research, 63:441-8, 2003, "*Expression of Differentiation Melanoma-Associated Antigen Genes is Associated with Favorable Disease Outcome in Advanced-Stage Melanomas*".

Takeuchi et al., J. Clinical Oncology, 22:2671-80, 2004, "*Prognostic Significance of Molecular Upstaging of Paraffin-Embedded Sentinel Lymph Nodes in Melanoma Patients*".

Voit et al., J. Clinical Oncology, 23:1218-1227, 2005, "*Molecular Staging in Stage II and III Melanoma Patients and its Effect on Long-Term Survival*".

Wascher et al., J. Clinical Oncology, 21:2558-63, 2003, "*Molecular Tumor Markers in the Blood: Early Prediction of Disease Outcome in Melanoma Patients Treated with a Melanoma Vaccine*".

Wascher et al., Clinical Cancer Research 9:1427-35, 2003, "*Stannicalcin-1: A Novel Molecular Blood and Bone Marrow Marker for Human Breast Cancer*".

Zehentner et al., Clinical Chemistry 50:2069-76, 2004, "*Mammaglobin as a Novel Breast Cancer Biomarker: Multigene Reverse Transcription-PCR Assay and Sandwich ELISA*".

International Search Report.

* cited by examiner

DETECTION OF CANCER CELLS IN BODY FLUIDS

RELATED APPLICATIONS

The present application is a continuation-in-part of prior U.S. patent application Ser. No. 10/713,808 filed on Nov. 14, 2003 now U.S. Pat. No. 7,910,295 which claims priority to U.S. Provisional Application Ser. No. 60/426,216 filed on Nov. 14, 2002. The present application also claims priority to U.S. Provisional Application Ser. No. 60/609,634 filed on Sep. 14, 2004. The contents of U.S. patent application Ser. No. 10/713,808, U.S. Provisional Application Ser. No. 60/426,216, and U.S. Provisional Application Ser. No. 60/609,634 are incorporated herein by reference.

FUNDING

This invention was made with support in part by grants from NIH National Cancer Institute P01 Grants CA 29605, Project II, and CA 12528, Project II. Therefore, the U.S. government has certain rights.

FIELD OF THE INVENTION

The present invention relates generally to cancer diagnosis, prognosis, and management. In particular, the invention relates to the detection of genetic markers indicative of melanoma, breast cancer, gastric cancer, pancreatic cancer, or colon cancer in body fluids. In one example, detection of multiple markers is achieved by quantitative real-time polymerase chain reaction.

BACKGROUND OF THE INVENTION

The metastasis of melanoma and carcinoma to distant sites often portends a poor prognosis (1). Assessment of primary and/or metastatic melanoma and carcinoma has been addressed in the new American Joint Committee on Cancer (AJCC) staging criteria (2, 3). The staging system, however, does not accurately take into account the disease progression events, particularly ongoing systemic metastasis, at the time patients are seen. The detection of melanoma or carcinoma cells in circulation is important in assessing tumor progression and potential for metastasis.

To date, only a limited number of tumor-associated markers have been identified that are absent in healthy cells but produced in melanoma or carcinoma cells. Heterogeneity of the expression of tumor genes and variable performance of the assays have posed major problems for detection of circulating tumor cells (CTCs) in blood. The clinical utility of molecular detection of circulating tumor cells in blood continues to be debated, mostly because of inconsistency among the previous findings, indicating the necessity for performing careful characterizations of these tests.

Melanoma and carcinoma patients are candidates for adjuvant therapy because of their high risk of disease recurrence after complete surgical resection. However, no current assays can accurately predict the survival of patients receiving neo-adjuvant or adjuvant biochemotherapy (BC).

SUMMARY OF THE INVENTION

The present invention provides new markers and new combinations of markers for detecting melanoma and carcinoma cells in body fluids. The invention also provides a quantitative, specific, sensitive, and reliable method for detecting circulating tumor cells in body fluids. This method is useful for cancer diagnosis, treatment, monitoring, and prognosis.

Melanoma

In one aspect, the invention features a method of detecting circulating melanoma cells in a subject. The method comprises obtaining a body fluid from a subject and detecting the expression of a panel of genes in the body fluid. The body fluid may be blood, bone marrow, cerebral spinal fluid, peritoneal fluid, or pleural fluid. The expression of the panel of genes indicates the presence of circulating melanoma cells in the subject.

In one embodiment, the panel of genes includes GalNAc-T ($\beta 1 \rightarrow 4$-N-acetylgalacto-saminyltransferase) or PAX-3 (paired box homeotic gene transcription factor 3). The panel of genes may further include one or more additional genes selected from the group consisting of GalNAc-T, MAGE-A3 (melanoma antigen gene-A3), MART-1 (melanoma antigen recognized by T cells-1), PAX-3, TRP-2 (tyrosinase-related protein-2), MITF (microphthalmia-associated transcription factor) and Tyrosinase. For example, the panel of genes may include PAX-3, MART-1, and MAGE-3; PAX-3, MART-1, and GalNAc-T; PAX-3, MAGE-3, and GalNAc-T; GalNAc-T, MAGE-A3, MART-1, and PAX-3; MART-1, GalNAc-T, MITF, and PAX-3; MART-1, TRP-2, GalNAc-T, and PAX-3; or Tyrosinase, MART-1, GalNAc-T, and PAX-3.

The invention further provides a method of detecting circulating melanomar cells in a subject, comprising obtaining a body fluid from a subject and quantifying the expression levels of a panel of genes using quantitative real-time reverse transcription polymerase chain reaction (qRT). The panel of genes includes at least three or four genes (any and every combination thereof) selected from the group consisting of GalNAc-T, MAGE-A3, MART-1, PAX-3, TRP-2, MITF, and Tyrosinase. For example, the panel of genes may include GalNAc-T, MAGE-A3, MART-1, and PAX-3. The expression of the panel of genes indicates the presence of circulating melanoma cells in the subject.

Among the panel of genes, at least one, two, three, or four of the genes (any and every combination thereof) is or are expressed. The expression of the panel of genes indicates that the subject is suffering from or at risk for developing a subclinical systemic melanoma. In accordance with the expression of the panel of genes, a health care provider can quantify the melanoma status; assign a clinical melanoma stage to the subject; predict treatment response, melanoma recurrence, or survival of the subject, e.g., for a period of at least three years (e.g., at least five years) following the removal of a primary tumor, sentinel lymphadenectomy (SLND), or both; monitor melanoma progression or treatment response; or select or randomize a treatment regime. In some cases, the body fluid or a tissue sample from the subject is histopathologically negative for melanoma cells, e.g., as determined by hematoxylin and eosin (H&E) or immunohistochemistry (IHC) staining.

The invention also provides a kit which can be used for detecting circulating melanoma cells in body fluids. The kit comprises a plurality of agents for detecting the expression of a panel of genes. In one embodiment, the panel of genes includes PAX-3 and one or more genes selected from the group consisting of GalNAc-T, MAGE-A3, MART-1, TRP-2, MITF, and Tyrosinase. For example, the panel of genes may include PAX-3, MART-1, and MAGE-3; PAX-3, MART-1, and GalNAc-T; PAX-3, MAGE-3, and GalNAc-T; GalNAc-T, MAGE-A3, MART-1, and PAX-3; MART-1, GalNAc-T, MITF, and PAX-3; MART-1, TRP-2, GalNAc-T, and PAX-3; or Tyrosinase, MART-1, GalNAc-T, and PAX-3.

Moreover, the invention features a kit comprising at least three or four pairs of primers for respectively quantifying the expression levels of at least three or four genes (any and every combination thereof) selected from the group consisting of GalNAc-T, MAGE-A3, MART-1, TRP-2, MITF, and Tyrosinase, as well as enzymes and reagents for performing qRT. For example, the kit may comprise at least four pairs of primers for respectively quantifying the expression levels of GalNAc-T, MAGE-A3, MART-1, and PAX-3.

Carcinoma

In another aspect, the invention features a method of detecting circulating breast, gastric, pancreatic, or colon cancer cells in a subject. The method comprises obtaining a body fluid from a subject and detecting the expression of a panel of genes in the body fluid. The body fluid may be blood, bone marrow, cerebral spinal fluid, peritoneal fluid, and pleural fluid. The expression of the panel of genes indicates the presence of circulating breast, gastric, pancreatic, or colon cancer cells in the subject.

In one embodiment, the panel of genes includes Stanniocalcin-1, Stanniocalcin-2, or HSP27 (heat shock protein 27). The panel of genes may further include one or more additional genes selected from the group consisting of C-Met (hepatocyte growth factor), MAGE-A3, Stanniocalcin-1, Stanniocalcin-2, mammaglobin (mammoglobulin), HSP27, GalNAc-T, CK20 (cytokeratin 20), and β-HCG (beta chain-human chorionic gonadotrophin).

In another embodiment, the panel of genes includes CK20, β-HCG and mammaglobin; GalNAc-T, mammaglobin, and β-HCG; mammaglobin, C-Met, GalNAc-T, and β-HCG; mammaglobin, β-HCG, HSP27, and C-Met; or HSP27, CK20, Stanniocalcin-1, and MAGE-A3.

The invention further provides a method of detecting circulating breast, gastric, pancreatic, or colon cancer cells in a subject, comprising obtaining a body fluid from a subject and quantifying the expression levels of a panel of genes using qRT. The panel of genes includes at least three or four genes (any and every combination thereof) selected from the group consisting of C-Met, MAGE-A3, Stanniocalcin-1, Stanniocalcin-2, mammaglobin, HSP27, GalNAc-T, CK20, and β-HCG. For example, the panel of genes may include a first combination of C-Met, MAGE-A3, GalNAc-T, and CK20; a second combination of mammaglobin, C-Met, GalNAc-T, and β-HCG; a third combination of mammaglobin, β-HCG, HSP27, and C-Met; or a fourth combination of HSP27, CK20, Stanniocalcin-1, and MAGE-A3. The expression of the panel of genes indicates the presence of circulating breast, gastric, pancreatic, or colon cancer cells in the subject.

Among the panel of genes, at least one, two, three, or four of the genes (any and every combination thereof) is or are expressed. The expression of the panel of genes indicates that the subject is suffering from or at risk for developing a subclinical systemic breast, gastric, pancreatic, or colon cancer. In accordance with the expression of the panel of genes, a health care provider can quantify the breast, gastric, pancreatic, or colon cancer status; assign a clinical breast, gastric, pancreatic, or colon cancer stage to the subject; predict treatment response, breast, gastric, pancreatic, or colon cancer recurrence, or survival of the subject, e.g., for a period of at least three years (e.g., at least five years) following the removal of a primary tumor, SLND, or both; monitor breast, gastric, pancreatic, or colon cancer progression or treatment response; or select or randomize a treatment regime. In some cases, the body fluid or a tissue sample from the subject is histopathologically negative for breast, gastric, pancreatic, or colon cancer cells, e.g., as determined by hematoxylin and eosin (H&E) or immunohistochemistry (IHC) staining.

The invention also provides a kit which can be used for detecting circulating breast, gastric, pancreatic, or colon cancer cells in body fluids. The kit comprises a plurality of agents for detecting the expression of a panel of genes. In one embodiment, the panel of genes includes Stanniocalcin-1, Stanniocalcin-2, or HSP27, and one or more additional genes selected from the group consisting of C-Met, MAGE-A3, Stanniocalcin-1, Stanniocalcin-2, mammaglobin, HSP27, GalNAc-T, CK20, and β-HCG.

In another embodiment, the panel of genes includes CK20, β-HCG and mammaglobin; GalNAc-T, mammaglobin, and β-HCG; mammaglobin, C-Met, GalNAc-T, and β-HCG; mammaglobin, β-HCG, HSP27, and C-Met; or HSP27, CK20, Stanniocalcin-1, and MAGE-A3.

Moreover, the invention features a kit comprising at least three or four pairs of primers for respectively quantifying the expression levels of at least three or four genes (any and every combination thereof) selected from the group consisting of C-Met, MAGE-A3, Stanniocalcin-1, Stanniocalcin-2, mammaglobin, HSP27, GalNAc-T, CK20, and β-HCG, as well as enzymes and reagents for performing qRT. For example, the kit may comprise at least four pairs of primers for respectively quantifying the expression levels of a first combination of C-Met, MAGE-A3, GalNAc-T, and CK20; a second combination of mammaglobin, C-Met, GalNAc-T, and β-HCG; a third combination of mammaglobin, β-HCG, HSP27, and C-Met; or a fourth combination of HSP27, CK20, Stanniocalcin-1, and MAGE-A3.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

Figure 1:
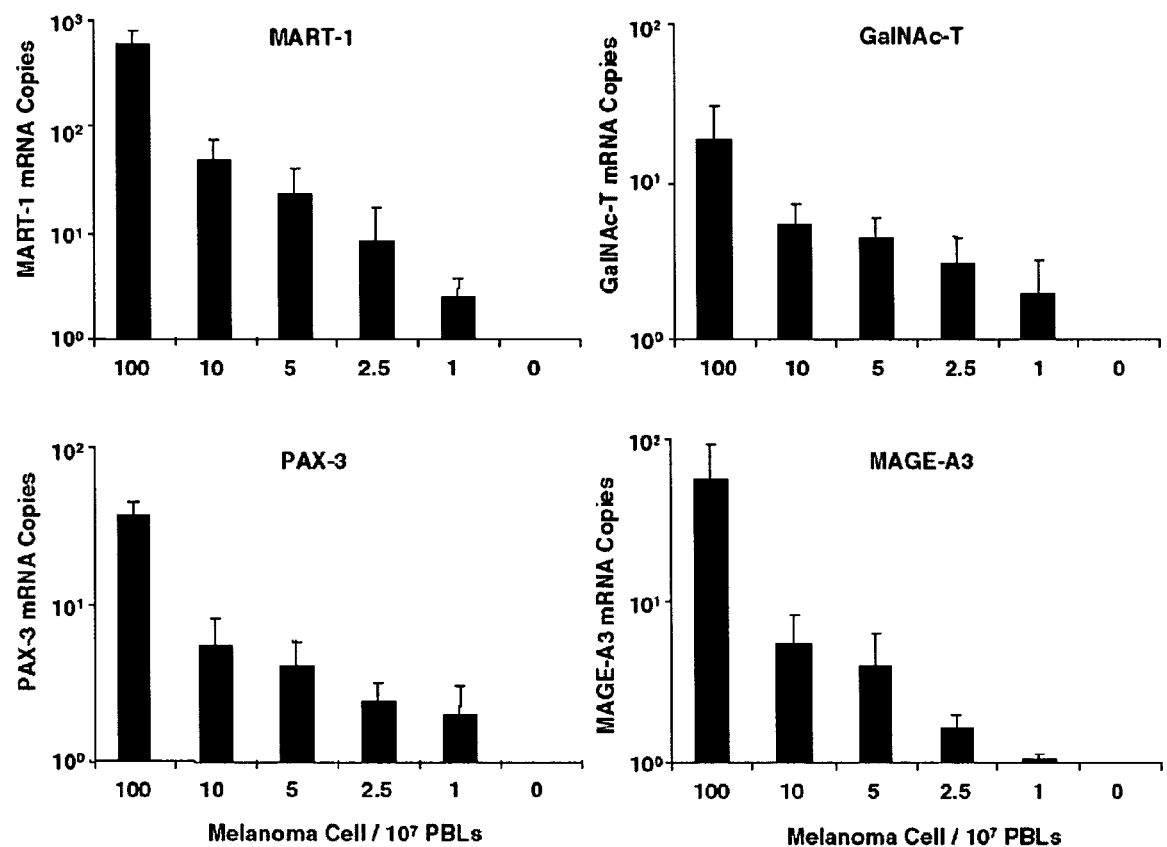
FIG. 1 shows qRT detection limits for melanoma cells mixed with peripheral blood leukocytes (PBLs) from healthy blood donors. Serially diluted melanoma cells (100, 10, 5, 2.5, 1, and 0) were mixed with $10^7$ PBLs from healthy blood donors. RNA was isolated from the cell mixture, and qRT was performed; the assay was performed 10 times. Mean (SD; error bars) absolute mRNA copies from a representative cell line (MA) are given according to the serial dilution.

The present invention is based on the unexpected discovery that multimarker qRT is a sensitive and specific quantitative assay to detect circulating melanoma cells in blood, that the number of positive markers in blood is significantly higher in patients with advanced stage melanoma than in patients with early stage disease, and that changes in multimarker detection in the blood of AJCC stage III melanoma patients receiving BC before and after surgery are correlated with disease progression and overall survival.

Accordingly, it is an object of the present invention to provide a method of detecting circulating cancer cells in a body fluid from a subject. In particular, the invention pertains to a multimarker assay for detecting cancer cells in a body fluid with high specificity and sensitivity. Quantification of the expression levels of the marker genes provides a powerful tool for diagnosis, prognosis, and treatment of cancer.

In its most general form, the method of the invention optionally comprises a step of identifying a candidate subject suffering from or at risk for developing cancer, with or without clinical evidence of the disease. Candidate identification can be in the judgment of the subject or a health care professional, and can be subjective (e.g., opinion) or objective (e.g., measurable by a test or diagnostic method). In some embodiments, the caner is melanoma, breast cancer, gastric cancer, pancreatic cancer, or colon cancer A "subject," as used herein, refers to human and non-human animals, including all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

The body fluid can be any fluid in which cancer cells may be present. Exemplary body fluids include blood, bone marrow, cerebral spinal fluid, peritoneal fluid, pleural fluid, lymph fluid, ascites, serous fluid, sputum, lacrimal fluid, stool, or urine. The body fluids can be collected using any of the methods well known in the art.

The method of the invention involves determination of the expression levels of cancer marker genes in a body fluid. A cancer "marker" is a gene whose expression is characteristic of a cancer cell, an mRNA transcribed from the marker gene, or a protein translated from the mRNA. While the present invention exemplifies several markers, any marker that is correlated with the presence of cancer cells in a body fluid may be used. For example, GalNAc-T, MAGE-A3, MART-1, PAX-3, TRP-2, MITF, Tyrosinase, C-Met, Stanniocalcin-1, Stanniocalcin-2, mammaglobin, HSP27, CK20, and β-HCG are markers useful for detecting melanoma or carcinoma cells in blood.

GalNAc-T catalyzes the transfer of N-acetylgalactosamine by β-1,4 linkage onto both gangliosides GM3 and GD3 to generate GM2 and GD2, respectively (U.S. Pat. No. 6,057, 105). It also catalyzes the transfer of N-acetylgalactosamine to other carbohydrate molecules such as mucins. Gangliosides are glycosphingolipids containing sialic acids which play an important role in cell differentiation, adhesion and malignant transformation. In melanoma, the expression levels of gangliosides GM2 and GD2 are often enhanced to very high levels and are associated with tumor progression including metastatic tumors. Gangliosides are also highly expressed in breast cancer cells. The gangliosides GM2 and GD2 are immunogenic in humans and can be used as a target for specific immunotherapy such as human monoclonal antibodies or cancer vaccines. GalNAc-T can be used as a marker of GM2 and GD2 expression and consequently a marker of either melanoma or breast cancer cells. GalNAc-T is generally not expressed in normal lymphocytes, epithelial cells, melanocytes, connective tissue, or lymph node cells. If detected, it is in very low levels.

MAGE-A3 and MART-1 are major melanocyte differentiation antigens that are immunogenic in patients and well expressed in melanoma (4, 5, 6). MAGE-A3 is a marker identified in melanoma and breast cancer cells and is a cytolytic T lymphocyte (CTL) target (7, 8). Clinical utilities of assessing MAGE-A3 mRNA expression in primary tumor, metastatic lesion, and blood in melanoma patients have been previously reported (8). MAGE-A3 is also expressed in many other tumors. MART-1 is frequently produced by melanoma cells and is not produced by nonmelanoma malignancies and lymph nodes from cancer-free patients (9).

PAX3 transcription factor has been reported to regulate melanin synthetic pathway via MITF expression (10). PAX3 is well expressed in human melanomas and contributes to melanoma cell survival (10; 11).

TRP-2 is a melanogenesis pathway enzyme. Although many of the melanogenic enzymes are absent from amelanotic melanomas, TRP-2 appears to be retained in many unpigmented melanomas. Recent studies have suggested that TRP-2 may be a good candidate for immunotherapy of amelanotic melanoma. In mouse, TRP-2 is encoded by the slaty locus. The enzyme catalyzes the rearrangement of DOPAchrome to the carboxylated derivative DHICA (5,6-dihydroxyindole-2-carboxylic acid). DHICA, in turn, is used in the synthesis of eumelanin (12).

MITF is a transcription factor.

Tyrosinase is a melanogenesis pathway enzyme involved in making melanin.

C-Met encodes a cell surface receptor to which the ligand, hepatocyte growth factor, binds and regulates cell functions. This receptor is frequently overexpressed in gastrointestinal cancers, including pancreatic carcinoma, and has been associated with tumor progression.

Stanniocalcin (STC) encodes a calcium- and phosphate-regulating hormone, a major antihypercalcemic hormone in fish. The hormone is produced in bony fish by the corpuscles of Stannius located close to the kidney. Recent results suggest that the biological repertoires of STCs in mammals are considerably larger than in fish and may not be limited to mineral metabolism. Stanniocalcin-1 is a recently discovered human gene that has been implicated in cellular calcium homeostasis and resistance to hypoxia and is located on chromosome 8p in a region associated with amplification in breast cancer (13). Stanniocalcin-2 has been identified as an estrogen-responsive gene differentially expressed between ER (estrogen receptor)-positive and ER-negative breast carcinomas (14).

Mammaglobin belongs to the uteroglobin gene family and is found on chromosome 11q12.3-13.1, a region frequently amplified in breast cancer. It relates to the secretion of the mammary gland and has been suggested to be a specific marker for detecting breast cancer cells (15).

HSP27 plays a role in the regulation of cell survival. In normal or unstressed cells, Hsp27 is constitutively expressed at a low level and, upon exposure to cytotoxic stimuli, its expression increases dramatically. Higher levels of Hsp27 expression are seen in a number of different cancers, including breast, ovarian, and prostate. Hsp27 protects cancer cells from apoptotic cell death and fosters resistance to drug treatment.

CK20 is a member of the intermediate filament protein family involved in cell structure and differentiation. Early immunological and Northern blot studies found that CK20 expression was restricted primarily to gastrointestinal tissue, transitional cell carcinoma, and Merkel cells. Recently, CK20 has been detected in samples from breast, thyroid, endometrial, lung, and pancreas carcinoma and oral squamous cell carcinoma (16).

β-HCG is produced by trophoblastic cells of placenta of pregnant woman and is essential for maintenance of pregnancy at the early stages. β-HCG is known to be produced by trophoblastic or germ cell origin tumors, such as choriocarcinoma or testicular carcinoma cells. Also, ectopic expression of β-HCG has been detected by a number of different immunoassays in various tumors of non-gonadal such as breast, lung, gastric, colon, and pancreas, etc. Although the function of β-HCG production in these tumors is still unknown, the atavistic expression of β-HCG by cancer cells and not by normal cells of non-gonadal origin suggests its usefulness in the detection of melanoma and breast cancer cells (U.S. Pat. No. 6,057,105).

Heterogeneity of the expression of tumor genes makes multimarker assays advantageous compared with single-marker assays for detecting circulating malignant cells (7, 17). Depending on the particular set of markers employed in a given analysis, the statistical analysis may vary. For example, where a particular combination of markers is highly specific for melanomas or breast cancer, the statistical significance of a positive result will be high. It may be, however, that such specificity is achieved at the cost of sensitivity, i.e., a negative result may occur even in the presence of melanoma or breast cancer. By the same token, a different combination may be very sensitive, but has a lower specificity.

As new markers are identified, different combinations may be developed that show optimal function with different ethnic groups or sex, different geographic distributions, different stages of disease, different degrees of specificity or different degrees of sensitivity. Marker combinations may also be developed, which are particularly sensitive to the effect of therapeutic regimens on disease progression. Patients may be monitored after surgery, hypothermia, immunotherapy, cytokine therapy, gene therapy, radiotherapy or chemotherapy, to determine if a specific therapy is effective.

The invention involves many different combinations of markers for the detection of cancer cells in body fluids. Any marker that is indicative of neoplasia in cancer cells may be included in this invention. For example, the combinations of at least three or four genes selected from the group consisting of GalNAc-T, MAGE-A3, MART-1, PAX-3, TRP-2, MITF, and Tyrosinase (e.g., PAX-3, MART-1, and MAGE-3; PAX-3, MART-1, and GalNAc-T; PAX-3, MAGE-3, and GalNAc-T; GalNAc-T, MAGE-A3, MART-1, and PAX-3; MART-1, GalNAc-T, MITF, and PAX-3; MART-1, TRP-2, GalNAc-T, and PAX-3; and Tyrosinase, MART-1, GalNAc-T, and PAX-3) are useful for detecting melanoma cells in blood; whereas the combinations of at least three or four genes selected from the group consisting of C-Met, MAGE-A3, Stanniocalcin-1, Stanniocalcin-2, mammaglobin, HSP27, GalNAc-T, CK20, and β-HCG (e.g., CK20, β-HCG and mammaglobin; GalNAc-T, mammaglobin, and β-HCG; mammaglobin, C-Met, GalNAc-T, and β-HCG; mammaglobin, β-HCG, HSP27, and C-Met; HSP27, CK20, Stanniocalcin-1, and MAGE-A3; and C-Met, MAGE-A3, GalNAc-T, and CK20) may be employed for the detection of breast, gastric, pancreatic, or colon cancer cells in blood.

Gene expression can be detected and quantified at mRNA or protein level using a number of means well known in the art. To measure mRNA levels, cells in fluid samples can be lysed and the levels of marker mRNA in the lysates or in RNA purified or semi-purified from the lysates determined by any of a variety of methods familiar to those in the art. Such methods include, without limitation, hybridization assays using detectably labeled marker-specific DNA or RNA probes and quantitative or semi-quantitative RT-PCR methodologies using appropriate marker gene-specific oligonucleotide primers. Alternatively, quantitative or semi-quantitative in situ hybridization assays can be carried out using, for example, unlysed cell suspensions, and detectably (e.g., fluorescently or enzyme-) labeled DNA or RNA probes. Additional methods for quantifying mRNA include RNA protection assay (RPA), cDNA and oligonucleotide microarrays, representation difference analysis (RDA), differential display, EST sequence analysis, and SAGE.

Methods of measuring protein levels in body fluids are also known in the art. Many such methods employ antibodies (e.g., monoclonal or polyclonal antibodies) that bind specifically to the target protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of test cells, and others (e.g., immunohistological methods or fluorescence flow cytometry) applied to unlysed cell suspensions. Methods of measuring the amount of label depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

In a preferred embodiment, marker gene expression in body fluids is detected and quantified using qRT where a fluorescent signal is produced proportional to the amount of a marker mRNA. qRT offers a robust, accurate, and less labor-intensive approach that allows rapid and reproducible quantitative analysis for detection of a few tumor cells in body fluids (9).

In qRT, template mRNA may be prepared by isolating mRNA or total RNA from body fluid samples using procedures well known in the art. For example, Tri-Reagent (Molecular Research Center) can be used to isolate total cellular RNA from blood samples. The amount and purity of the isolated RNA can be assessed by ultraviolet spectrophotometry. For comparison, a control RNA sample may be prepared, for example, from a biological fluid from a normal person.

Next, the template mRNA is converted into a complementary DNA (cDNA) by reverse transcriptase using an oligo dT primer, a marker-specific primer, or random oligomers. The two commonly used reverse transcriptases are avian myeloblastosis virus reverse transcriptase (AMV-RT) and Moloney murine leukaemia virus reverse transcriptase (MMLV-RT).

The cDNA is then amplified by PCR (polymerase chain reaction), as described in detail in U.S. Pat. Nos. 4,683,195, 4,683,202 and 4,800,159, as well as in Innis et al., 1990 (18). Briefly, two primer sequences are prepared which are complementary to regions on opposite complementary strands of the marker sequence. An excess of deoxynucleoside triphosphates are added to a reaction mixture along with a DNA polymerase, e.g., Taq polymerase. The primers bind to the marker and the polymerase causes the primers to be extended along the marker sequence by adding on nucleotides. By raising and lowering the temperature of the reaction mixture, the extended primers dissociate from the marker to form reaction products, excess primers bind to the marker and to the reaction products and the process is repeated.

A PCR primer is any nucleic acid capable of priming the synthesis of a nascent nucleic acid in a template-dependent process. Typically, primers are oligonucleotides from ten to twenty nucleotides in length, but longer sequences can be employed. Primers may be provided in double-stranded or single-stranded form, although the single-stranded form is preferred.

Selection of primers is based on a variety of different factors, depending on the method of amplification and the specific marker involved. For example, the choice of primer will determine the specificity of the amplification reaction. The primer needs to be sufficiently long to specifically hybridize to the marker nucleic acid and allow synthesis of amplification products in the presence of the polymerization agent and under appropriate temperature conditions. Shorter primer molecules generally require cooler temperatures to form sufficiently stable hybrid complexes with the marker nucleic acid.

Primer sequences do not need to correspond exactly to the specific marker sequence. Non-complementary nucleotide fragments may be attached to the 5' end of the primer with the remainder of the primer sequence being complementary to the template. Alternatively, non-complementary bases can be interspersed into the primer, provided that the primer sequence has sufficient complementarily, in particular at the 3' end, with the template for annealing to occur and allow synthesis of a complementary DNA strand.

In some embodiments, primers may be designed to hybridize to specific regions of a marker nucleic acid sequence. For example, GC rich regions are favored as they form stronger hybridization complexes than AT rich regions.

In most cases, it will be preferable to synthesize desired oligonucleotides. Suitable primers can be synthesized using commercial synthesizers, such as those supplied by Applied Biosystems (Foster City, Calif.) using methods well known to those of ordinary skill in the art. Where double-stranded primers are desired, synthesis of complementary primers is performed separately and the primers mixed under conditions permitting their hybridization.

The application of fluorescence techniques to RT-PCR, together with suitable instrumentation capable of combining amplification, detection and quantification, has led to the development of kinetic RT-PCR methodologies that are revolutionizing the possibilities for quantifying nucleic acids (19). These instruments (e.g., ABI Prism 7700, Perkin-Elmer-Applied Biosystems, Foster City, Calif., USA; Lightcycler, Roche Molecular Biochemicals, Mannheim, Germany; and iCycler iQ Real-Time Thermocycler Detection System, Bio-Rad Laboratories) are run as closed-tube systems and quantification requires no post-amplification manipulation. This avoids problems of contamination, results in short turnaround times for data acquisition and analysis and minimizes hands-on time. The entire process, starting at the reverse transcription and ending with full quantification, is automated, which makes these instruments ideally suited for high-throughput screening applications.

There are a number of techniques (e.g., molecular beacons, DNA-binding dyes, hybridization probes, and hydrolysis probes) available for detecting amplified product with about the same sensitivity. They use fluorescent dyes and combine the processes of amplification and detection of an RNA target to permit the monitoring of PCR reactions in real-time; their high sensitivity eliminates the need for a second-round amplification, and decreases opportunities for generating false-positive results. The simplest method uses fluorescent dyes that bind specifically to double-stranded-DNA. Some other methods rely on the hybridization of fluorescence-labeled probes to the correct amplicon.

The concept of the threshold cycle (Ct) is at the heart of accurate and reproducible quantification using fluorescence-based RT-PCR. Fluorescence values are recorded during every cycle and represent the amount of product amplified to that point in the amplification reaction. The more template present at the beginning of the reaction, the fewer number of cycles it takes to reach a point in which the fluorescent signal is first recorded as statistically significant above background. This point is defined as the Ct, and will always occur during the exponential phase of amplification. Therefore, quantification is not affected by any reaction components becoming limited in the plateau phase, which results in a systematic bias against the more abundant templates and makes any quantification based on measurements of overall product yield intrinsically unreliable.

The reporter signal is normalized to the fluorescence of an internal reference dye (e.g., Taqman) or between the three dyes (e.g., Lightcycler), to allow for corrections in fluorescent fluctuations caused by changes in concentration or volume, and a Ct value is reported for each sample. This value can be translated into a quantitative result by constructing a standard curve.

Standard curves using fluorescence are easily generated, thanks to the linear response over a large dynamic range. Quantification of mRNA transcription can be either relative or absolute. Relative quantification determines the changes in steady-state transcription of a gene and is often adequate. A relative standard consists of a sample, the calibrator, which is used to create a dilution series with arbitrary units. The calibrator can be any nucleic acid, as long as its concentration and length of amplicon are known. During the RT-PCR assay, the target Ct is compared directly with the calibrator Ct and is recorded as containing either more or less mRNA. In contrast, absolute quantification of transcription allows the precise determination of copy number per cell, total RNA concentration, or unit mass of tissue. It requires the construction of an absolute standard curve for each individual amplicon to ensure accurate reverse transcription and PCR amplification profiles.

An absolute standard curve can be prepared, for example, by subcloning the amplicon behind a T7 or SP6 RNA polymerase promoter in a plasmid vector. An in vitro-transcribed sense RNA transcript is generated, the sample is digested with RNAse-free DNAse and the RNA is quantified accurately. It is important to ensure that the standard RNA template is a single, pure species free from DNA contamination. Triplicate measurements of its concentration are taken on a spectrophotometer such as Genequant II (Amersham Pharmacia Biotech, Little Chalfont, UK) and the absorbance is converted to a "target copy number per µg RNA." The standard curve is generated by performing three independent serial dilutions of the RNA standard and assaying each dilution in duplicate, together with positive and negative control reactions. To maximize accuracy, the dilutions should be made over the range of copy numbers that include the amount of target mRNA expected in the experimental RNA samples. The high and low Ct values are discarded to correct for pipetting error and the remaining four values are averaged to give the final Ct value for that dilution. The Ct value is inversely proportional to the log of the initial copy number. Therefore, a standard curve is generated by plotting the Ct values, with 95% confidence intervals, against the logarithm of the initial copy numbers. The copy numbers of experimental RNAs can be calculated after real-time amplification from the linear regression of that standard curve.

In another method, single-stranded sense-strand oligodeoxynucleotides is used as an alternative to the T7-RNA polymerase-generated standard amplicon. The advantage of using a single-stranded sense oligodeoxynucleotide is that it significantly simplifies the process of obtaining a standard curve for amplicons up to 100 bp, which encompasses most real-time RT-PCR amplicons.

The accepted method for correcting sample-to-sample variation is to amplify, simultaneously with the target, a cellular RNA that serves as an internal reference against which other RNA values can be normalized. The ideal internal standard should be expressed at a constant level among different tissues of an organism, at all stages of development, and should be unaffected by the experimental treatment. In addition, an endogenous control should also be expressed at roughly the same level as the RNA under study. The mRNAs specifying the housekeeping genes glyceraldehyde-3-phosphate-dehydrogenase (GAPDH), β-actin and ribosomal RNAs (rRNA) are most commonly used to normalize patterns of gene expression, although other mRNAs (e.g., histone H3 and cyclophilin) have been used occasionally.

Analysis of the expression levels of the marker genes is useful for cancer diagnosis, prognosis, and management of the disease. The expression of the marker genes in a body fluid indicates that circulating cancer cells are present in the subject.

As shown in Example 1 below, qRT assays for the mRNA of four melanoma-associated markers: MART-1, GalNAc-T, PAX-3, and MAGE-A3 were developed. In optimization studies, 17 melanoma cell lines and 49 PBL samples from volunteers were tested. RNA and melanoma cell dilution studies were performed to assess the detection limits and imprecision of the assays. The mRNAs in blood specimens from 94 melanoma patients (AJCC stage I, n=20; II, n=20; III, n=32; IV, n=22) were measured. All markers were frequently detected in melanoma cell lines, whereas none of the markers was detected in PBLs from normal volunteers. The qRT assay could detect 1 melanoma cell in $10^7$ PBLs in the melanoma cell-dilution studies. Markers were detected in 15%, 30%, 75%, and 86% of melanoma patients with AJCC stage I, II, III, and IV disease, respectively. The number of positive markers and AJCC stage were significantly correlated (Spearman correlation coefficient=0.58; $P<0.0001$).

In Example 2, blood specimens were collected at four sampling points from 63 patients enrolled in a prospective multicenter phase II trial of BC before and after surgical treatment of AJCC stage III melanoma. Each specimen was assessed by qRT for expression of four melanoma-associated markers: MART-1, GalNAc-T, PAX-3, and MAGE-A3, and the changes of CTCs during treatment and prognostic effect of CTCs after overall treatment on recurrence and survival were investigated. At a median postoperative follow-up time of 30.4 months, 44 (70%) patients were clinically disease-free. In relapse-free patients, the number of detected markers significantly decreased during preoperative BC ($P=0.036$), during postoperative BC ($P=0.002$), and during overall treatment ($P<0.0001$). Marker detection after overall treatment was associated with significant decreases in relapse-free and overall survival (OS) ($P<0.0001$). By multivariate analysis using a Cox proportional hazard model, the number of markers detected after overall treatment was a significant independent prognostic factor for OS (risk ratio=12.6; 95% CI, 3.16 to 50.5; $P=0.0003$).

Therefore, multimarker qRT can detect circulating melanoma cells in blood. Measurement of the studied molecular markers in blood is useful in detection of metastasis and monitoring treatment response of melanoma patients. Furthermore, multimarker mRNA detection can be used to predict the presence of systemic subclinical disease, and changes in marker detection during and after treatment can be used as a surrogate predictor of treatment outcome.

Accordingly, the invention provides methods for quantifying the melanoma status, assigning a clinical melanoma stage to the subject, predicting treatment response, melanoma recurrence, or survival of the subject (e.g., for a period of at least three years following the removal of a primary tumor, SLND, or both), monitoring melanoma progression or treatment response, selecting or randomizing a treatment regime.

A diagnostic method of the invention involves obtaining a body fluid sample from a subject and detecting the expression of a panel of marker genes as described above. If one or more of the genes is or are expressed, the subject is diagnosed as being suffering from or at risk for developing a subclinical systemic melanoma. The disease stage can be determined according to the expression levels of the marker genes, e.g., the number of marker genes expressed and/or the amount of each marker mRNA. In general, a high number of expressed marker genes indicates an advanced disease stage (e.g., AJCC stages III or IV).

This invention also provides a logistically practical assay to monitor cancer progression. The most significant advantage of this approach compared to other approaches is the ability to monitor disease progression without assessing the tumor. This is particularly important during early phases of distant disease spread, in which subclinical disease is undetectable by conventional imaging techniques. To monitor the progression of a cancer, mRNA or total RNA is isolated from a body fluid from a subject suffering from cancer. The expression of a panel of marker genes is analyzed. The expression levels of the marker genes is indicative of cancer progression. Generally, an increased or high number of expressed marker genes indicates progression of the cancer.

The invention further provides a method of determining the efficacy of a cancer therapy. A therapy is administered to a patient suffering from cancer, and a biological fluid is obtained from the patient. mRNA or total RNA is isolated from the fluid, and the expression of a panel of marker genes is assessed. The expression levels of the marker genes is indicative of whether the efficacy of the therapy is good or poor. For example, an increased or high number of expressed marker genes indicates that the therapy is bad, whereas a decreased or low number of expressed marker genes indicates that the therapy is good.

Because the methods described above require only RNA extraction from a bodily fluid such as blood, it can be performed at any time and repeatedly on a single patient. Blood can be taken and monitored before or after surgery; before, during, and after treatment, such as chemotherapy, radiation therapy, gene therapy or immunotherapy; or during follow-up examination after treatment for disease progression, stability, or recurrence.

Further, the invention provides predictive measures of response to cancer therapies and mortality. More specifically, the invention provides a method of predicting the probability of survival of a subject suffering from cancer. The method comprises providing a body fluid sample from the subject and detecting the expression of a panel of gene markers in the sample. The expression levels of the marker genes are indicative of the possibility of cancer relapse and the survival of the patient. An decreased or low number of expressed marker genes indicates that the subject is more likely to be relapse-free and/or to survive.

Moreover, the invention provides a method of predicting the possible response of a cancer patient to a therapy. The method comprises the steps of obtaining a body fluid sample from a patient and detecting the expression of a panel of marker genes in the sample. The expression levels of the marker genes is indicative of whether the patient is likely to respond to a cancer therapy. An decreased or low number of expressed marker genes indicates that the subject is more likely to be responsive to the cancer therapy.

All the basic essential materials and reagents required for detecting cancer cells in a body fluid sample can be assembled together in a kit. The kit may generally comprise agents (e.g., pre-selected primers) specific for a panel of marker genes. Also included may be enzymes suitable for amplifying nucleic acids including various polymerases (reverse transcriptase, Taq, etc.), deoxynucleotides and buffers to provide the necessary reaction mixture for amplification. Such kit may further comprise, in suitable means, distinct containers for each individual reagent and enzyme as well as for each marker primer pair. Kits of the present invention may include a means for containing the reagents in close confinement for commercial sale such as, e.g., injection or blow-molded plastic containers into which the desired reagent are retained. Other containers suitable for conducting certain steps of the disclosed methods also may be provided.

In particular, a kit for detecting circulating melanoma cells in body fluids may comprise a plurality of agents (e.g., primers for quantifying marker mRNA using qRT) for detecting the expression of a panel of genes, including PAX-3 and one or more genes selected from the group consisting of GalNAc-T, MAGE-A3, MART-1, TRP-2, MITF, and Tyrosinase. For example, the kit may comprise a plurality of agents for detecting the expression of PAX-3, MART-1, and MAGE-3; PAX-3, MART-1, and GalNAc-T; PAX-3, MAGE-3, and GalNAc-T; GalNAc-T, MAGE-A3, MART-1, and PAX-3; MART-1, GalNAc-T, MITF, and PAX-3; MART-1, TRP-2, GalNAc-T, and PAX-3; or Tyrosinase, MART-1, GalNAc-T, and PAX-3.

Alternatively, the kit may comprise a plurality of agents for detecting the expression of at least three genes selected from the group consisting of GalNAc-T, MAGE-A3, MART-1, PAX-3, TRP-2, MITF, and Tyrosinase, as well as enzymes and reagents for performing qRT. For example, the kit may comprise at least four pairs of primers for respectively quantifying the expression levels of GalNAc-T, MAGE-A3, MART-1, and PAX-3.

A kit for detecting circulating breast, gastric, pancreatic, or colon cancer cells in body fluids may comprise a plurality of agents (e.g., primers for quantifying marker mRNA using qRT) for detecting the expression of a panel of genes including Stanniocalcin-1, Stanniocalcin-2, or HSP27, and one or more additional genes selected from the group consisting of C-Met, MAGE-A3, Stanniocalcin-1, Stanniocalcin-2, mammaglobin, HSP27, GalNAc-T, CK20, and β-HCG. Alternatively, the panel of genes may include at least three or four genes selected from the group consisting of C-Met, MAGE-A3, Stanniocalcin-1, Stanniocalcin-2, mammaglobin, HSP27, GalNAc-T, CK20, and β-HCG. For example, the panel of genes may include CK20, β-HCG and mammaglobin; GalNAc-T, mammaglobin, and β-HCG; mammaglobin, C-Met, GalNAc-T, and β-HCG; mammaglobin, β-HCG, HSP27, and C-Met; or HSP27, CK20, Stanniocalcin-1, and MAGE-A3.

Specifically, the kit may comprise at least three or four pairs of primers for respectively quantifying the expression levels of at least three or four genes selected from the group consisting of C-Met, MAGE-A3, Stanniocalcin-1, Stanniocalcin-2, mammaglobin, HSP27, GalNAc-T, CK20, and β-HCG, as well as enzymes and reagents for performing qRT. For example, the kit may comprise at least four pairs of primers for respectively quantifying the expression levels of a first combination of C-Met, MAGE-A3, GalNAc-T, and CK20; a second combination of mammaglobin, C-Met, GalNAc-T, and β-HCG; a third combination of mammaglobin, β-HCG, HSP27, and C-Met; or a fourth combination of HSP27, CK20, Stanniocalcin-1, and MAGE-A3.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

Multimarker Quantitative Real-Time PCR Detection of Circulating Melanoma Cells in Peripheral Blood: Relation to Disease Stage in Melanoma Patients Materials and Methods Melanoma Cell Lines Seventeen melanoma cell lines (MA, MB, MC, MD, ME, MF, MG, MH, MI, MJ, MK, ML, MM, MN, MO, MP, and MQ) were established and characterized at the John Wayne Cancer Institute (JWCI). Cells were grown in RPMI 1640 containing 100 mL/L heat-inactivated fetal calf serum and 10 g/L penicillin/streptomycin (Gibco) in a T75-cm$^2$ flask and were used when they reached 70%-80% confluence.

Patients

All patients enrolled in the study had documented physical and medical histories, and their AJCC stage of disease was determined and recorded at the time of blood drawing. Blood was drawn from 94 melanoma patients (20 with stage I, 20 with stage II, 32 with stage III, and 22 with stage IV disease) immediately before they received any treatment at JWCI. All patients signed consents for the use of their blood specimens, and the study was carried out according to the guidelines set forth by the Saint John's Health Center and the JWCI Institutional Review Board committee.

The study was conducted in a double-blinded fashion: the patients' disease status was not known to the individuals who performed the PCR assay or analyzed the PCR data, and PCR results were not known to the individuals who recorded disease status.

Blood Processing and RNA Extraction

We collected 10 mL of blood from each patient with melanoma. Blood samples were collected in sodium citrate-containing tubes, and the first several milliliters of blood at the initial venipuncture were discarded to eliminate skin-plug contamination, as described previously (17, 8). Within 2 h after being drawn, blood was processed in a designated blood-processing room. Blood cells were collected by use of Purescript RBC Lysis Solution (Gentra), according to the manufacturer's instructions.

Tri-Reagent (Molecular Research Center) was used to isolate total cellular RNA from blood samples and cell lines, as described previously (8, 20). All of the RNA extraction procedures were performed in a designated sterile laminar flow hood with RNase-free labware. RNA was quantified and assessed for purity by ultraviolet spectrophotometry. Blood processing, RNA extraction, RT-PCR assay set up, and post-RT-PCR product analysis were carried out in separate designated rooms to prevent cross-contamination (17, 21).

Primers and Probes

Primer and probe sequences were designed for the qRT as described previously (9, 21). The fluorescence resonance energy transfer probe sequences were as follows: MART-1, 5'-FAM-TGCAGAACAGTCACCACCACC-BHQ-1-3' (SEQ ID NO:1); GalNAc-T, 5'-FAM-ATGAGGCT-GCTTTCACTATCCGCA-BHQ-1-3' (SEQ ID NO:2); PAX-3, 5'-FAM-CCAGACTGATTACGCGCTCTCCC-BHQ-1-3' (SEQ ID NO:3); MAGE-A3, 5'-FAM-AGCTCCTGCCCA-CACTCCCGCCTGT-BHQ-1-3' (SEQ ID NO:4); and glyceraldehyde-3-phosphate dehydrogenase (GAPDH), 5'-FAM-CAGCAATGCCTCCTGCACCACCAA-BHQ-1-3' (SEQ ID NO:5), where FAM is 6-carboxyfluorescein and BHQ-1 is Black Hole Quencher 1.

Melanoma cells and 49 PBL samples from healthy donors were used to optimize the assay. The GAPDH gene was used as a control housekeeping gene. Any specimen with insufficient GAPDH mRNA was excluded from the study.

Multimarker qRT Assay

Reverse transcription reactions were performed with Moloney murine leukemia virus reverse transcriptase (Promega) with oligo(dT) primer (8, 9). The multimarker qRT assay was performed in an iCycler iQ Real-Time Thermocycler Detection System (Bio-Rad Laboratories). We transferred 5 uL of cDNA from 250 ng of total RNA to a well of a 96-well PCR plate (Fisher Scientific) in which 0.5 uM each primer, 0.3 uM fluorescence resonance energy transfer probe, 1 U of AmpliTaq Gold polymerase (Applied Biosystems), 200 uM each deoxynucleotide triphosphate, 4.5 mM $MgCl_2$, and PCR buffer were added to a final volume of 25 uL. Samples were amplified with a precycling hold at 95° C. for 10 min, followed by 42 cycles of denaturation at 95° C. for 1 min, annealing for 1 min (at 55° C. for GAPDH, 59° C. for MART-1, 62° C. for GalNAc-T and PAX-3, and 58° C. for MAGE-A3), and extension at 72° C. for 1 min. The calibration curve was generated with the threshold cycle (Ct) of 9 serial dilutions of plasmid templates ($10^8$-$10^0$ copies). The Ct of each sample was interpolated from the calibration curve, and the number of mRNA copies was calculated by the iCycler iQ Real-Time Detection System Software (Bio-Rad Laboratories). Each assay was performed at least twice and included marker-positive (melanoma cell lines) and -negative controls (PBLs of healthy donors) and reagent controls (reagent alone without RNA or cDNA) for qRT assays to verify the results. The mean number of mRNA copies for each gene was used for analysis.

Serial Dilution Study of Melanoma Cells in PBLs

To determine the detection limit for melanoma cells in blood, we performed qRT on serially diluted melanoma cells mixed with PBLs from healthy blood donors. This in vitro model system to some extent mimics the circulating melanoma cells in blood. In the assay, serial dilutions of melanoma cells (100, 10, 5, 2.5, 1, and 0 cells) that expressed all four markers were mixed with $10^7$ donor-derived PBLs and assayed for each marker by qRT. This in vitro assay was performed 10 times to validate the reproducibility and robustness of the assay system.

Plasmid Controls

Specific plasmid controls were synthesized as described previously (21). PCR products generated from MART-1, GalNAc-T, PAX-3, MAGE-A3, and GAPDH were run on 2% agarose gel electrophoresis and extracted by the QIAquick gel extraction method (Qiagen) according to the manufacturer's instructions. Extracted PCR products were ligated into pCR II-TOPO cloning vector (Invitrogen) and transformed into *Escherichia coli* DH5-α cells. Plasmids containing the target gene were purified and quantified for use in the quantitative PCR setup. To confirm that the inserted PCR product size was correct, plasmids were digested with specific restriction enzymes, and the products were visualized after gel electrophoresis.

Statistical Analysis

We used the Mann-Whitney U-test to compare positive marker detection among AJCC stages. The Pearson correlation coefficient and Cochran-Armitage trend test were used to examine the significance of associations of the number of markers and AJCC stage of disease. Kappa analysis was used to assess the relationship between two markers. Spearman correlation coefficients were used to assess the relationship between multimarker detection and AJCC stage. All two-sided P values $\leq 0.05$ were considered statistically significant.

Results

Calibration Curves and Assay Variation

The calibration curves showed the expected linear increase of signal with logarithm of the copy number. PCR efficiency, assessed from the slopes of the curves, was between 90% and 100%. The correlation coefficients for all calibration curves (Ct vs log copy number) in the study were $\geq 0.99$.

When qRT was performed in different experiments with mRNA from one melanoma cell line, the imprecision values (CVs) for GAPDH, MART-1, GalNAc-T, PAX-3, and MAGE-A3 were 7.7%, 21%, 14%, 27%, and 34%, respectively between assays (n=3) and 1.8%-22% for triplicate results (intra-assay variation).

Multimarker mRNA Expression in Melanoma Cell Lines

All melanoma cell lines showed GAPDH expression with high copy numbers (mean, $1.6\times10^7$; range, $1.7\times10^6$ to $5.5\times10^7$), and expression of the mRNA markers MART-1, GalNAc-T, PAX-3, and MAGE-A3 was detected in 88%, 100%, 100%, and 94%, respectively, of these melanoma cell lines. The numbers of MART-1 mRNA copies ranged from 0 to $8.4\times10^6$ (mean, $1.2\times10^6$) per 250 ng of total RNA from individual melanoma lines. The copy numbers of GalNAc-T ranged from $9.4\times10^1$ to $1.5\times10^5$ (mean, $2.2\times10^4$), PAX-3 ranged from $3.2\times10^3$ to $2.7\times10^6$ (mean, $2.0\times10^5$), and MAGE-A3 ranged from 0 to $3.3\times10^5$ (mean, $7.3\times10^4$). Fourteen cell lines expressed all 4 markers, and 3 lines expressed 3 markers. No marker expression was detected in PBLs from 49 healthy donors under the optimum conditions established for individual markers.

qRT Detection Limit of Marker Expression

After establishing potential marker genes for melanoma, we used RNA dilution series to determine the detection limit of each marker. Total RNA was isolated from melanoma cell lines that expressed all 4 markers; we then performed qRT on RNA serially diluted from $2.5\times10^{-1}$ to $10^{-8}$ ug for individual markers. The assay was performed several times with three different cell lines. Although mRNA concentrations differed among cell lines, the instrument-qRT assay combination detected all markers consistently at picogram concentrations: MART-1, PAX-3, and MAGE-A3 expression from 1 pg of RNA and GalNAc-T from 10 pg of RNA above background. The background subtraction was obtained from the net (inner-outer) fluorescence for each well, and threshold fluorescence for the experiment was set at 10 times the mean of the SD of the fluorescence of each well from cycles 2 to 10 by the iCycler iQ Real-Time Detection System Software. Linear regression analysis of curves from serial RNA dilutions demonstrated that the correlation coefficient was 0.95-0.998 and slopes were −3.50 to −3.75 for individual markers with r=0.95–0.998. GAPDH expression was detected from 0.01 pg of RNA in all cell lines assessed.

qRT Detection Limit for Melanoma Cells Mixed with PBLs in vitro

The assay detected mRNA for each marker from 1 melanoma cell mixed with 107 PBLs; mRNA copies gradually decreased on serial dilution of melanoma cells (FIG. 1). The number of mRNA copies for individual markers varied. All markers were positive at 10 melanoma cells mixed with $10^7$ PBLs in all 10 experiments. Detection frequencies of MART-1, GalNAc-T, PAX-3, and MAGE-A3 from 1 melanoma cell mixed with 107 PBLs were 90%, 80%, 50%, and 20%, respectively. These rates are equivalent to 1 melanoma cell in several milliliters of blood. When we tested dilutions of 1 melanoma cell in 108 PBLs, we detected expression of MART-1, GalNAc-T, PAX-3, and MAGE-A3 in 6, 4, 2, and 2 of 10 attempts, respectively.

Assessment of Multimarker mRNA Detection in Blood from Melanoma Patients

Figure 2:
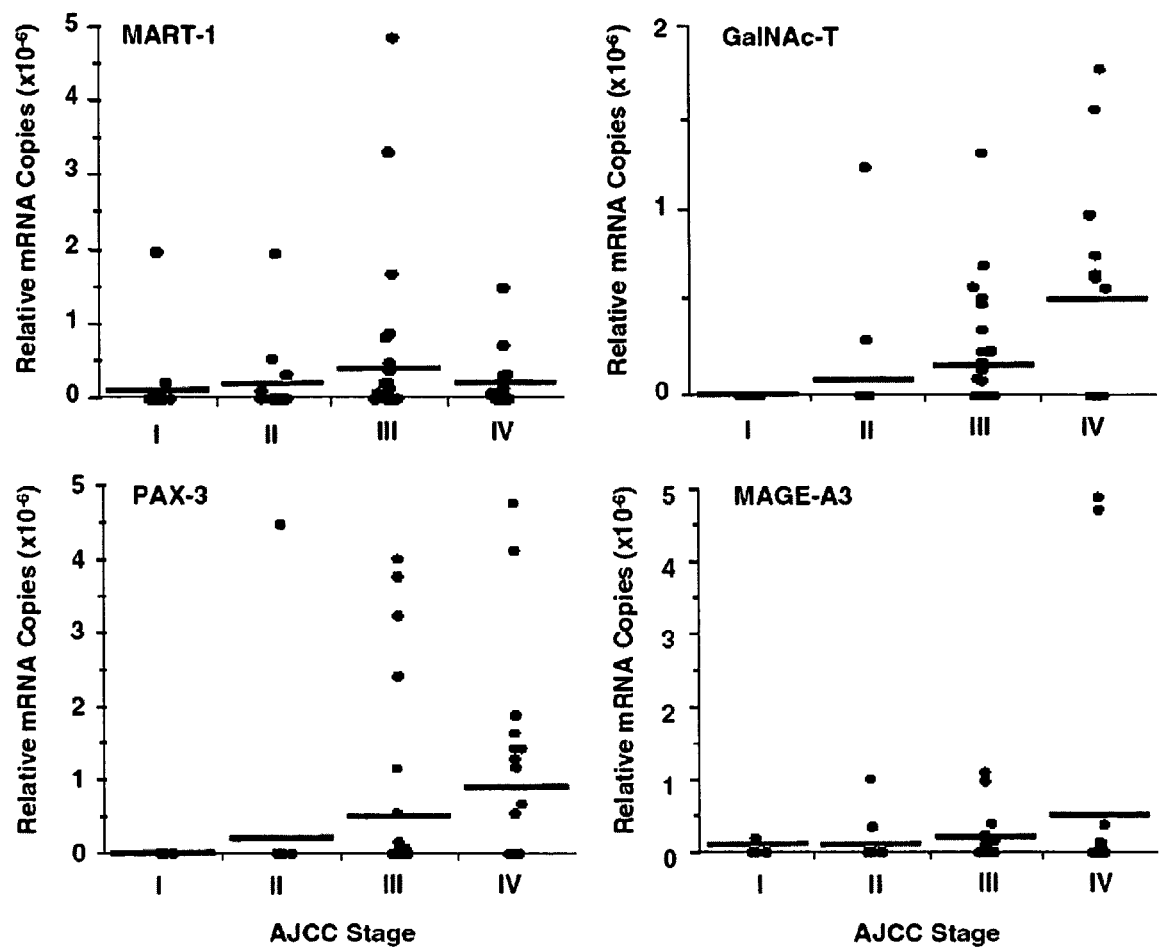
FIG. 2 shows qRT quantification of cancer markers in peripheral blood of melanoma patients. Blood specimens were collected from patients with different AJCC stages of melanoma. RNA was isolated from total cells in blood, and qRT was performed. Relative mRNA copies are given according to the AJCC stage. Pearson correlation analysis indicates significant correlations between AJCC stage and relative mRNA copies for all markers: MART-1, $P=0.0071$; GalNAc-T, $P=0.0002$; PAX-3, $P<0.0001$; MAGE-A3, $P=0.014$. Horizontal bars indicate mean mRNA copies.

The range of relative mRNA copies (absolute mRNA copies of each marker/absolute mRNA copies of GAPDH) was $10^{-6}$ to $10^{-8}$ for each marker (FIG. 2). The relative number of mRNA copies was higher at a higher disease stage. Pearson correlation coefficient analysis results were significant between AJCC stage and relative mRNA copies for all markers: r=0.28 (P=0.01) for MART-1; r=0.37 (P=0.0002) for GalNAc-T; r=0.28 (P<0.0001) for PAX-3; r=0.25 (P=0.014) for MAGE-A3. Relative mRNA copies for patients with stage III/IV disease (metastatic disease) were significantly higher (Mann-Whitney U-test) than for patients with stage I/II disease (localized disease) for all individual markers (MART-1, P=0.01; GalNAc-T, P=0.0002; PAX-3, P=0.0001; MAGE-A3, P=0.03).

Overall, in blood samples from 94 melanoma patients, MART-1, GalNAc-T, PAX-3, and MAGE-A3 were detected in 30%, 24%, 22%, and 18% of patients, respectively (Table 1), with lower detection rates of marker genes in patients with early-stage disease. The detection rate for each marker was significantly related (Cochran-Armitage trend test) to AJCC stage (MART-1, P=0.003; GalNAc-T, P=0.0006; PAX-3, P<0.0001; MAGE-A3, P=0.016). We found no significant coincidence (kappa test) of marker detection between pairs of marker genes other than MART-1 and MAGE-A3 (P=0.021).

TABLE 1 mRNA detection in blood from melanoma patients

| Marker | AJCC stage, n (%) | | | | | |
| --- | --- | --- | --- | --- | --- | --- |
| | I (n = 20) | II (n = 20) | III (n = 32) | IV (n = 22) | Total (n = 94) | p[a] |
| MART-1 | 2 (11) | 4 (20) | 11 (34) | 11 (50) | 28 (30) | 0.003 |
| GalNAc-T | 0 (0) | 2 (10) | 13 (41) | 8 (36) | 23 (24) | 0.0006 |
| PAX-3 | 0 (0) | 1 (5) | 10 (31) | 10 (45) | 21 (22) | <0.0001 |
| MAGE-A3 | 1 (5) | 2 (10) | 7 (22) | 7 (32) | 17 (18) | 0.016 |

[a]Comparison between AJCC stage and each marker detection by Cochran-Armitage trend test.

The number of multimarkers detected in patients was also higher in those with higher AJCC stage (Spearman r=0.58; P<0.0001; Table 2). Only 3 (15%) of 20 AJCC stage I patients had at least 1 positive marker detected, whereas 19 (86%) of 22 AJCC stage IV patients had at least 1 positive marker and 12 (55%) of 22 AJCC stage IV patients had multiple markers detected. When patients were divided into those with no or 1 positive marker detected and those with 2 or more (multiple) positive markers detected, the Cochran-Armitage trend test indicated a significant increase of patients with multiple markers detected who had advanced stages of disease (P<0.0001). The number of markers detected showed a sharp contrast in distribution between stages I/II and III/IV. In stages I/II, 15%, 7%, 0%, and 0% of patients had 1, 2, 3, and 4 markers detected, respectively. On the other hand, 35%, 28%, 15%, and 2% of patients had 1, 2, 3, and 4 markers detected, respectively, in stage III/IV. There was a significant difference in multimarker detection between AJCC stages I/II and III/IV (P<0.0001).

TABLE 2

Number of markers correlated to disease stage.

| Markers detected, n | AJCC stage, n (%) | | | | | |
| --- | --- | --- | --- | --- | --- | --- |
| | I (n = 20) | II (n = 20) | III (n = 32) | IV (n = 22) | Total (n = 94) | P |
| 0 | 17 (85) | 14 (70) | 8 (25) | 3 (14) | 42 (45) | <0.0001[a] |
| 1 | 3 (15) | 3 (15) | 12 (37) | 7 (32) | 25 (26) | |
| 2 | 0 (0) | 3 (15) | 7 (22) | 8 (36) | 18 (19) | |
| 3 | 0 (0) | 0 (0) | 5 (16) | 3 (14) | 8 (9) | |
| 4 | 0 (0) | 0 (0) | 0 (0) | 1 (5) | 1 (1) | |
| ≦1 | 20 (100) | 17 (85) | 20 (63) | 10 (45) | 67 (71) | <0.0001[b] |
| ≧2 | 0 (0) | 3 (15) | 12 (37) | 12 (55) | 17 (29) | |

[a]Spearman correlation coefficient analysis showed a significant correlation between number of positive markers and AJCC stage.
[b]Cochran-Armitage trend test showed a significant increase of patients with more than 2 positive markers detected in advanced stage of disease.

Discussion

In this study, we demonstrated the usefulness of multimarker qRT as a sensitive and specific quantitive assay to detect circulating melanoma cells in blood. In vitro models showed the reproducibility and reliability of the assay and the feasibility of clinical application. The assay detected ~1 melanoma cell in $10^7$-$10^8$ PBLs from healthy blood donors. The number of positive markers in blood was significantly higher in patients with advanced stage melanoma than in patients with early-stage disease.

The qRT assay has high-throughput capacity that can analyze large numbers of samples without PCR product carry-over contamination. Moreover, this assay enables accurate and reproducible quantification of mRNA to compare gene expression among samples. This assay system offers an all logistic advantage because it can detect occult metastatic tumor cells among millions of healthy leukocytes in blood without requiring cell-separation methods such as magnetic beads, separation medium, or other approaches.

The 4 mRNA markers selected in the study were frequently found in melanoma cells but not in healthy donor blood PBLs under the optimized assay conditions. Our previous studies demonstrated that metastatic melanoma tumors are heterogeneous in melanoma-associated marker expression (9, 21). Because MART-1, GM2/GD2, and MAGE-A3 have been demonstrated to be highly immunogenic in humans (22-24), cells expressing these antigens may be deleted by host immunity. However, the combination of markers in the multimarker assay can compensate for individual marker expression; thus, we expect detection of tumor cells to be increased and false negative results reduced.

In blood specimens from patients with melanoma, the overall detection rate in blood was highest for MART-1, similar for GalNAc-T and PAX-3, and lowest for MAGEA3. Differences in cell line analysis compared with blood may be related to the physiology of cells during circulation in blood or the clonal phenotype (17). Detection rates of the multimarker qRT assay were higher than any of the individual markers alone. These findings support the supposition that a single-marker assay in blood has limited clinical utility (17, 25, 26). We did not use tyrosinase in the study because of previously reported variable detection rates and potential problems with false positives (25, 26). The detection of tumor cells in blood has often been tested directly in correlation with outcome in previously reported studies. However, such analyses must be carried out in defined patient specimens because many variables play a role in tumor metastasis (17). Blood markers can serve both diagnostic and predictive functions. In this study, predictive markers for clinical stage II patients were validated through molecular upstaging of sentinel lymph nodes (SLNs) (9, 21). Previously we have shown the significance of circulating melanoma cells in prediction of disease outcome in patients with stage III/IV melanoma (27, 28). In the present study, we quantitatively demonstrated the differences in blood from patients with AJCC stages I/II and III/IV disease. Potentially this quantitative real-time assay of circulating cells could be useful for assessing patient disease status and guiding treatment management (29, 30).

In summary, melanoma prognosis is currently determined based on tumor and host demographic and static factors, but dynamic factors of ongoing tumor metastasis are also important. Molecular markers in blood can be a very informative indicator of systemic disease progression. Our findings suggest the potential clinical usefulness of the qRT assay for detecting circulating cells in blood of melanoma patients.

Example 2

Serial Monitoring of Circulating Melanoma Cells during Neoadjuvant Biochemotherapy for Stage III Melanoma: Outcome Prediction in a Multicenter Trial Patients and Methods Patients Patients for this qRT study were selected from 94 melanoma patients enrolled in a prospective multicenter trial of neoadjuvant BC. The 94 patients comprised 61 males and 33 females with a median age of 43 years (range, 17-76). All patients were pathologically diagnosed with AJCC stage III melanoma and treated with neoadjuvant BC and surgery between 1999 and 2002. A subset of patients from three of centers, John Wayne Cancer Institute (Santa Monica, Calif.), University of Colorado Cancer Center (Aurora, Colo.), and Hubert H. Humphrey Cancer Center (Robbinsdale, Minn.), signed informed consent for the use of their blood specimens, and the qRT study was approved and carried out in accordance with guidelines set forth by the individual institutional review board committees.

Treatment Program and Blood Procurement

All patients received two cycles of BC at three-week intervals before surgery. The BC regimen comprised cisplatin, 20 mg/m$^2$, intravenously (i.v.), on day 1-4; dacarbazine, 800 mg/m$^2$, i.v., on day 1; vinblastine, 1.6 mg/m$^2$, i.v., on day 1-4; interleukin-2 (Chiron Corporation, Emeryville, Calif.), 9 MU/m$^2$, i.v. over 24 hours, on day 1-4; α-interferon (Schering-Plough, Madison, N.J.), 5 MU/m$^2$, subcutaneously (s.c.), on day 1-5; and granulocyte-colony-stimulating factor (Amgen Inc., Thousand Oaks, Calif.), 5 mcg/kg, s.c., on day 6-12. Patients then underwent therapeutic lymphadenectomy and began two cycles of BC within 42 days after surgery; the postoperative BC regimen was the same as the preoperative regimen. All patients were clinically and radiologically evaluated at specified time points during treatment and follow-up.

Peripheral blood was drawn immediately before preoperative BC (pre-BC, n=63), before surgery (pre-surgery, n=55), after surgery (post-surgery, n=55), and after postoperative BC (post-BC, n=58). The interval between each of the four sampling times was approximately six weeks, and all blood specimens were processed within 30 hours after drawing.

Standard Operation Procedure

Ten milliliter of blood samples were collected in sodium citrate-containing tubes, and the first several milliliters were discarded to eliminate skin-plug contamination, as previously described (8, 17). All blood specimens were then coded by a computer-generated number, so that the qRT study could be conducted in a blinded fashion. Total cells in blood were collected using the Purescript RBC Lysis Solution (Gentra, Minneapolis, Minn.), following the manufacturer's instruction.

Tri-Reagent (Molecular Research Center, Cincinnati, Ohio) was used to isolate total cellular RNA from blood specimens, as previously described (8, 17). RNA was quantified and assessed for purity by ultraviolet spectrophotometry. Blood processing, RNA extraction, RT-PCR assay set-up, and post RT-PCR product analysis were carried out in separate designated rooms to prevent cross-contamination.

RT reactions were performed using Moloney murine leukemia virus reverse transcriptase (Promega, Madison, WI) with oligo-dT primer (8, 9). Multimarker qRT assay was performed using iCycler iQ RealTime Thermocycler Detection System (Bio-Rad Laboratories, Hercules, CA) as previously described (31, 9). Primer and probe sequences were designed for the qRT. Fluorescence resonance energy transfer probe sequences were as follows: MART-1, 5'-FAM-TGCA-GAACAGTCACCACCACC-BHQ-1-3' (SEQ ID NO:1); GalNAc-T, 5'-FAM-ATGAGGCTGCTTTCACTATC-CGCA-BHQ-1-3' (SEQ ID NO:2); PAX-3, 5'-FAM-CCA-GACTGATTACGCGCTCTCCC-BHQ-1-3' (SEQ ID NO:3); MAGE-A3, 5'-FAM-AGCTCCTGCCCACACTC-CCGCCTGT-BHQ-1-3' (SEQ NO:4); and glyceraldehyde-3-phosphate dehydrogenase (GAPDH), 5'-FAM-CAGCAAT-GCCTCCTGCACCACCAA-BHQ-1-3' (SEQ ID NO:5). We transferred 5 pL cDNA from 250 ng total RNA to a well of a 96-well PCR plate (Fisher Scientific, Pittsburgh, Pa.), in which 0.5 μmol/L of each primer, 0.3 μmol/L probe, 1 U AmpliTaq Gold polymerase (Applied Biosystems, Branchburg, N.J.), 200 μmol/L of each dNTP, 4.5 mmol/L MgCl$_2$ and PCR buffer were applied, to a final volume of 25 μL. Samples were amplified with a precycling hold at 95° C for 10 min, followed by 42 cycles of denaturation at 95° C for 1 min, annealing at 55° C for 1 min for GAPDH (annealing at 59° C. for MART-1, at 62° C for GalNAc-T and PAX-3, and at 58° C for MAGE-A3), and extension at 72° C. for 1 min.

The standard curve was generated by using threshold cycle (Ct) of nine serial dilutions of plasmid templates ($10^0$ to $10^8$ copies). The Ct of each sample was interpolated from the standard curve, and the number of mRNA copies was calculated by the iCycler iQ RealTime Detection System Software (Bio-Rad Laboratories). Seventeen melanoma cell lines and peripheral blood leukocytes (PBLs) from 49 healthy donors were used to optimize the assay. Each qRT assay was performed at least twice and included marker-positive (melanoma cell lines) and marker-negative controls (PBLs of healthy donors), and reagent controls (reagent alone without RNA or cDNA). GAPDH gene was used as a control housekeeping gene. Any specimen with inadequate GAPDH mRNA was excluded from the study. The mean mRNA copy number was used for analysis.

Statistical Analysis

This study was designed to investigate the changes on CTCs during treatment course and prognostic effect of circulating tumor burden after overall treatment on disease relapse and survival. The primary outcomes were the number of markers detected after overall treatment, relapse of the disease, and survival. The mRNA copies and the detection rate of individual markers at each time point were considered as secondary endpoints.

The detection of individual marker at each time point was tabulated. Wilcoxon signed rank test was used to compare the number of markers during treatment. Mann-Whitney U test was used to assess the difference of markers between relapse and relapse-free patients. Relapse-free survival (RFS) after lymphadenectomy and OS from the start of BC (pre-BC) were used for outcome measurement. Cox proportional hazard model was developed to examine the association of markers detected with RFS and OS, and used for multivariate analysis. Known clinical and pathological risk factors, such as age, gender, primary tumor site, Breslow tumor thickness, ulceration, AJCC primary tumor (T) stage, regional lymph node (N) stage, stage III grouping (IIIA, IIIB, and IIIC), previous treatment status, detection of individual markers and number of multimarker after overall treatment were included in the model. Stepwise method was used for prognostic variable selection. Log-rank test was used to compare RFS and OS among patients with individual marker detection and patients with 0, 1, and $\geqq 2$ detectable markers after overall treatment. Survival curves were generated using Kaplan-Meier method.

For the secondary outcomes, McNemar's test was used to compare the detection of individual marker between any two time points, and Wilcoxon signed rank test was used to examine the change of mRNA copies during treatment course. The analysis was performed using SAS statistical software and all tests were two-sided with significance level $\leqq 0.05$.

Results

Eligible Patients for qRT Study

Our qRT study included 63 of the 94 patients enrolled in the clinical trial; the remaining 31 patients were excluded because of lack of blood procurement (23 patients), rapid disease progression (four patients), or severe toxicity during neoadjuvant BC (four patients). Multimarker qRT assay was performed on 231 blood samples collected from the 63 patients (41 males and 22 females; median age, 42 years [range, 17-76 years]; median postoperative follow-up, 30.4 months).

Standard Curves and Specificity of Multimarker qRT Assay

The standard curves showed the expected linear increase of signal with logarithm of the copy number. PCR efficiency assessed from the slopes of the curves was between 90 and 100%. The correlation coefficient for all standard curves in the study was $\geqq 0.99$. MART-1, GalNAc-T, PAX-3, and MAGE-A3 mRNA were not detected in blood specimens from the 49 healthy donors under the optimized conditions, but were frequently detected in melanoma cell lines (31). Individual markers were detected in one to five melanoma cells diluted in $10^7$ PBLs of healthy donors; the coefficient of variation (CV) was 1.8 to 22% for triplicate results (intra-assay variation) and 14 to 34% between assays for individual markers (31).

Change in Multimarker mRNA Detection During Treatment

Figure 3:
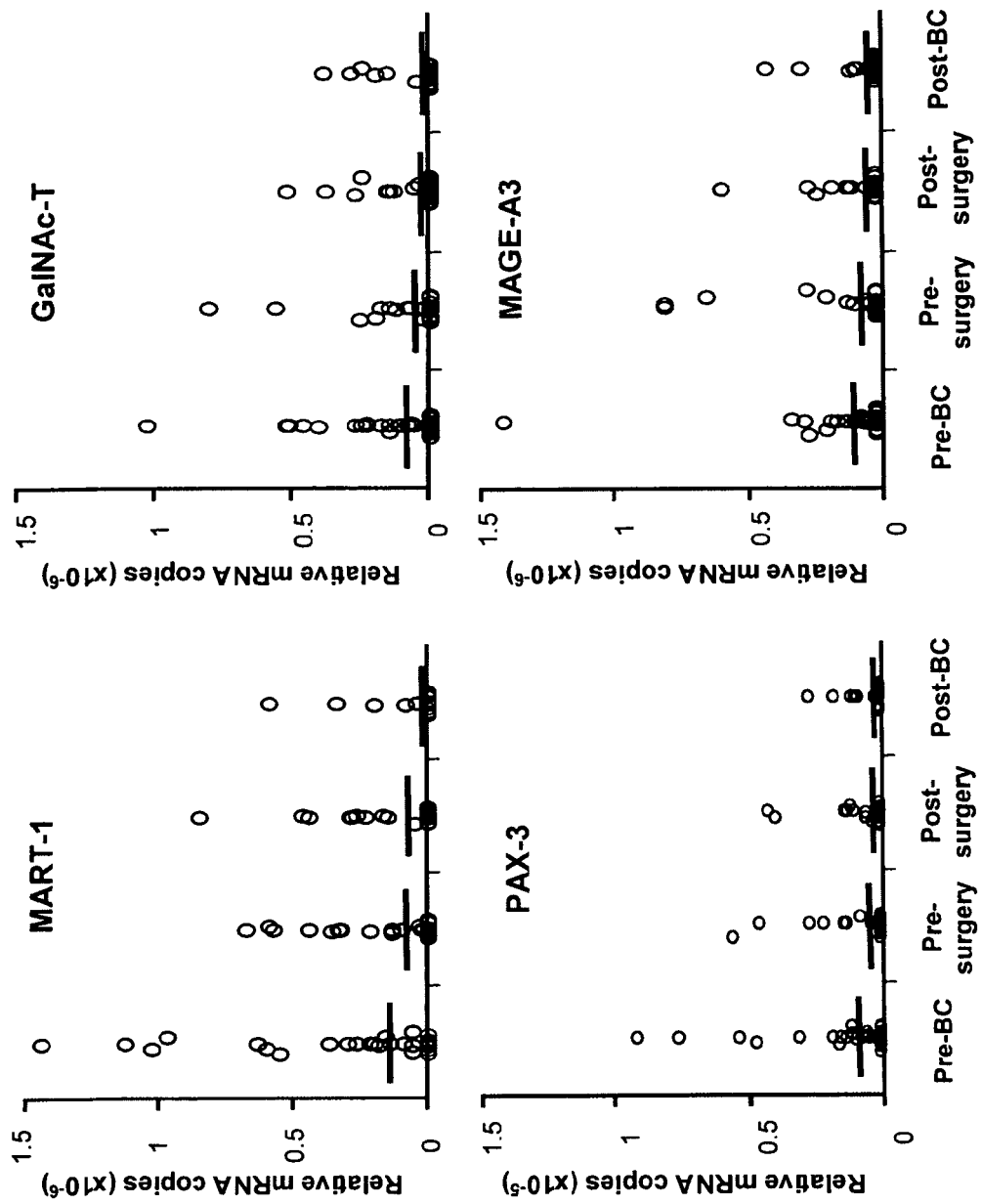
FIG. 3 shows copy levels of individual mRNA markers in blood specimens obtained before, during, and after treatment. The relative mRNA copy number of each marker after treatment was significantly lower than its copy number before treatment: MART-1, $P=0.0006$; GalNAc-T, $P=0.005$; PAX-3, $P=0.002$; MAGE-A3, $P=0.013$. Bars show mean copy numbers.

GAPDH expression was detected in all blood specimens; absolute copy number per 250 ng total RNA ranged from $9.21 \times 10^4$ to $1.83 \times 10^8$ (median, $1.75 \times 10^7$). The range of relative mRNA copies (absolute mRNA copies of each marker/absolute mRNA copies of GAPDH) was 0 to $8.4 \times 10^{-6}$ overall and $10^{-8}$ to $10^{-6}$ for marker-positive specimens (FIG. 3). During treatment relative mRNA copies of all markers gradually decreased to levels significantly below pretreatment levels (MART-1, P=0.0006; GalNAc-T, P=0.005; PAX-3, P=0.002; MAGE-A3, P=0.013). Changes in relative mRNA copy level during each sampling interval were not significant, except for a significant decrease in PAX-3 mRNA copy level during preoperative BC (P=0.032).

Similarly, individual marker detection rates dropped significantly during overall treatment (MART-1, P=0.001; GalNAc-T, P=0.005; PAX-3, P=0.001; MAGE-A3, P=0.004), reflecting a gradual, nonsignificant decrease during each sampling interval (Table 3). The number of markers detected in each specimen also decreased significantly during overall treatment (P<0.0001), reflecting significant decreases during preoperative and postoperative BC (P=0.046 and P=0.008, respectively) but not during surgery. Before treatment, blood specimens from 47 (75%) of 63 patients expressed at least one marker and specimens from 22 (36%) patients expressed more than one marker. After overall treatment, specimens from 41 (70%) patients had no markers and only five (10%) specimens expressed more than one marker.

TABLE 3

Detection of Markers in Blood Sampled at Specific Intervals during Treatment

| | Pre-BC Patients (n = 63) | (%) | Pre-surgery Patients (n = 55) | (%) | Post-surgery Patients (n = 55) | (%) | Post-BC Patients (n = 58) | (%) | P* |
|---|---|---|---|---|---|---|---|---|---|
| Marker | | | | | | | | | |
| MART-1 | 23 | (37) | 15 | (27) | 10 | (18) | 5 | (9) | .001 |
| GalNAc-T | 18 | (29) | 12 | (22) | 10 | (18) | 6 | (10) | .005 |
| PAX-3 | 23 | (37) | 11 | (20) | 11 | (20) | 7 | (12) | .001 |
| MAGE-A3 | 22 | (35) | 10 | (18) | 11 | (20) | 7 | (12) | .004 |
| Number of Markers Detected | | | | | | | | | |
| 0 | 16 | (25) | 25 | (46) | 22 | (40) | 41 | (70) | <.0001 |
| 1 | 25 | (39) | 16 | (29) | 26 | (47) | 12 | (20) | |
| 2 | 6 | (10) | 10 | (18) | 5 | (9) | 3 | (6) | |
| 3 | 15 | (24) | 4 | (7) | 2 | (4) | 1 | (2) | |
| 4 | 1 | (2) | 0 | (0) | 0 | (0) | 1 | (2) | |

Abbreviations: BC, biochemotherapy.
*P value calculated using McNemar's test for each marker and Wilcoxon signed rank test for number of markers.

Multimarker mRNAs as a Predictor of Disease Relapse and Survival

At a median postoperative follow-up of 30.4 months (range 4.6 to 52.4 months), 19 (30%) of 63 patients had relapsed and 44 (70%) were clinically disease-free. After treatment, marker detection rate after treatment clearly distinguished relapse and relapse-free patient groups (61% and 15%, respectively). The number of markers was significantly lower in relapse-free patients (P=0.001), reflecting a significant overall decrease (P<0.0001) and significant decreases during preoperative and postoperative BC (P=0.036 and P<0.0001, respectively) (Table 4). In patients with relapse, there was no significant difference between any two sampling points; 18 (95%) of 19 patients expressed at least one marker during treatment and those who expressed at least two markers after treatment developed relapse within seven months (Table 5).

TABLE 5

Marker Detection and Duration of RFS in Patients with Relapse

| | Number of Markers Detected | | | | |
|---|---|---|---|---|---|
| Patient | Pre-BC | Pre-Surgery | Post-Surgery | Post-BC | RFS (months) |
| 1 | 0 | NA | NA | 3 | 2.80 |
| 2 | 1 | 1 | 0 | 0 | 20.50 |
| 3 | 1 | 0 | 1 | 1 | 31.30 |
| 4 | 1 | 1 | 1 | 0 | 44.10 |
| 5 | 0 | 1 | 0 | NA | 28.23 |
| 6 | 1 | 3 | 1 | 1 | 12.56 |
| 7 | 2 | 0 | 1 | 0 | 23.90 |
| 8 | 3 | 0 | 0 | 1 | 14.73 |
| 9 | 0 | 3 | 1 | 1 | 6.93 |
| 10 | 3 | 0 | 0 | 1 | 9.60 |

TABLE 4

Multimarker Detection Correlated with Disease Outcome

| Number of Marker Detected | Pre-BC Patients | (%) | Pre-surgery Patients | (%) | Post-surgery Patients | (%) | Patients | (%) | P* |
|---|---|---|---|---|---|---|---|---|---|
| No Relapse (n = 44) | | | | | | | | | |
| 0 | 12 | (27) | 17 | (44) | 17 | (42) | 34 | (85) | <.0001 |
| 1 | 15 | (34) | 12 | (31) | 19 | (48) | 5 | (13) | |
| 2 | 5 | (12) | 9 | (23) | 3 | (8) | 1 | (2) | |
| 3 | 12 | (27) | 1 | (2) | 1 | (2) | 0 | (0) | |
| 4 | 0 | (0) | 0 | (0) | 0 | (0) | 0 | (0) | |
| Relapse (n = 19) | | | | | | | | | |
| 0 | 4 | (21) | 8 | (50) | 5 | (33) | 7 | (39) | .8 |
| 1 | 10 | (53) | 4 | (25) | 7 | (47) | 7 | (39) | |
| 2 | 1 | (5) | 1 | (6) | 2 | (13) | 2 | (10) | |
| 3 | 3 | (16) | 3 | (19) | 1 | (7) | 1 | (6) | |
| 4 | 1 | (5) | 0 | (0) | 0 | (0) | 1 | (6) | |

Abbreviations: BC, biochemotherapy.
*P value calculated using Wilcoxon signed rank test.

TABLE 5-continued

Marker Detection and Duration of RFS in Patients with Relapse

| | Number of Markers Detected | | | | |
|---|---|---|---|---|---|
| Patient | Pre-BC | Pre-Surgery | Post-Surgery | Post-BC | RFS (months) |
| 11 | 1 | 1 | 1 | 1 | 31.67 |
| 12 | 1 | 0 | 3 | 4 | 6.57 |
| 13 | 4 | 0 | 2 | 0 | 14.37 |
| 14 | 1 | 2 | NA | 0 | 28.70 |
| 15 | 1 | 0 | 2 | 1 | 22.83 |
| 16 | 1 | 0 | 1 | 2 | 5.83 |
| 17 | 0 | NA | NA | 0 | 13.03 |
| 18 | 1 | 3 | NA | 2 | 3.87 |
| 19 | 3 | NA | 0 | 0 | 8.90 |

Abbreviations: RFS, relapse-free survival; BC, biochemotherapy; NA, not applicable.

Figure 4:
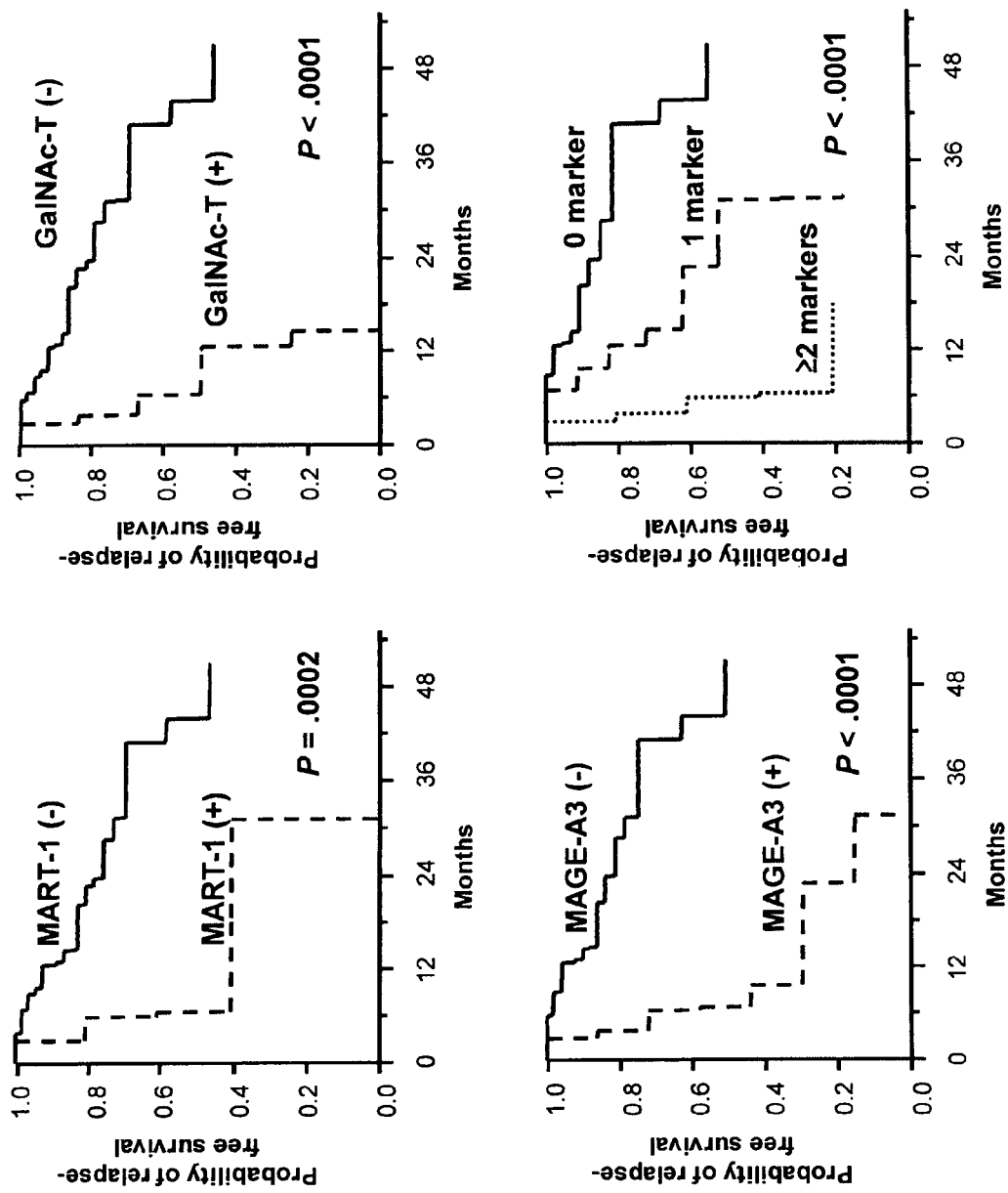
FIG. 4 shows Kaplan-Meier curves of Relapse-free survival (RFS) based on marker detection after the treatment.

Before treatment, marker detection had no correlation with gender, age, primary site, Breslow tumor thickness, ulceration, pT stage, pN stage, stage III grouping (IIIA, IIIB, and IIIC), and previous treatment status. After treatment, RFS significantly decreased when blood specimens were positive for MART-1, GalNAc-T, and/or MAGE-A3 (P=0.0003, P<0.0001, and P<0.0001, respectively) (FIG. 4). The size of the decrease was directly correlated with the number of positive markers (P<0.0001) (FIG. 4). For patients with no positive markers (n=41), 7 patients had relapsed, and the estimated RFS rates were 97.6±2.4% (estimate±SE) for 12 months and 89.8±4.9% for 24 months. For patients with one positive marker (n=12), 7 had relapsed, and the estimated RFS rates were 81.8±11.6% for 12 months and 62.3±15.0% for 24 months. For patients with ≧2 positive markers (n=5), 4 had relapsed, and the estimated RFS rates was 20.0±17.9% for 12 months. Cox proportional hazard model analysis selected the detection of MART-1 (risk ratio=10.2; 95% CI=1.91 to 54.1; P=0.007), GalNAc-T (risk ratio=6.56; 95% CI=1.43 to 30.0; P=0.015), and MAGE-A3 (risk ratio=33.6; 95% CI, 7.82 to 144.6; P<0.0001) after overall treatment as the significant prognostic factors for RFS. No other factors were selected in Cox proportional model except age (>50 vs ≦50) (risk ratio=8.25; 95% CI, 2.01 to 33.8; P=0.003). Marker detection in blood specimens obtained before or during treatment was not correlated with RFS.

Figure 5:
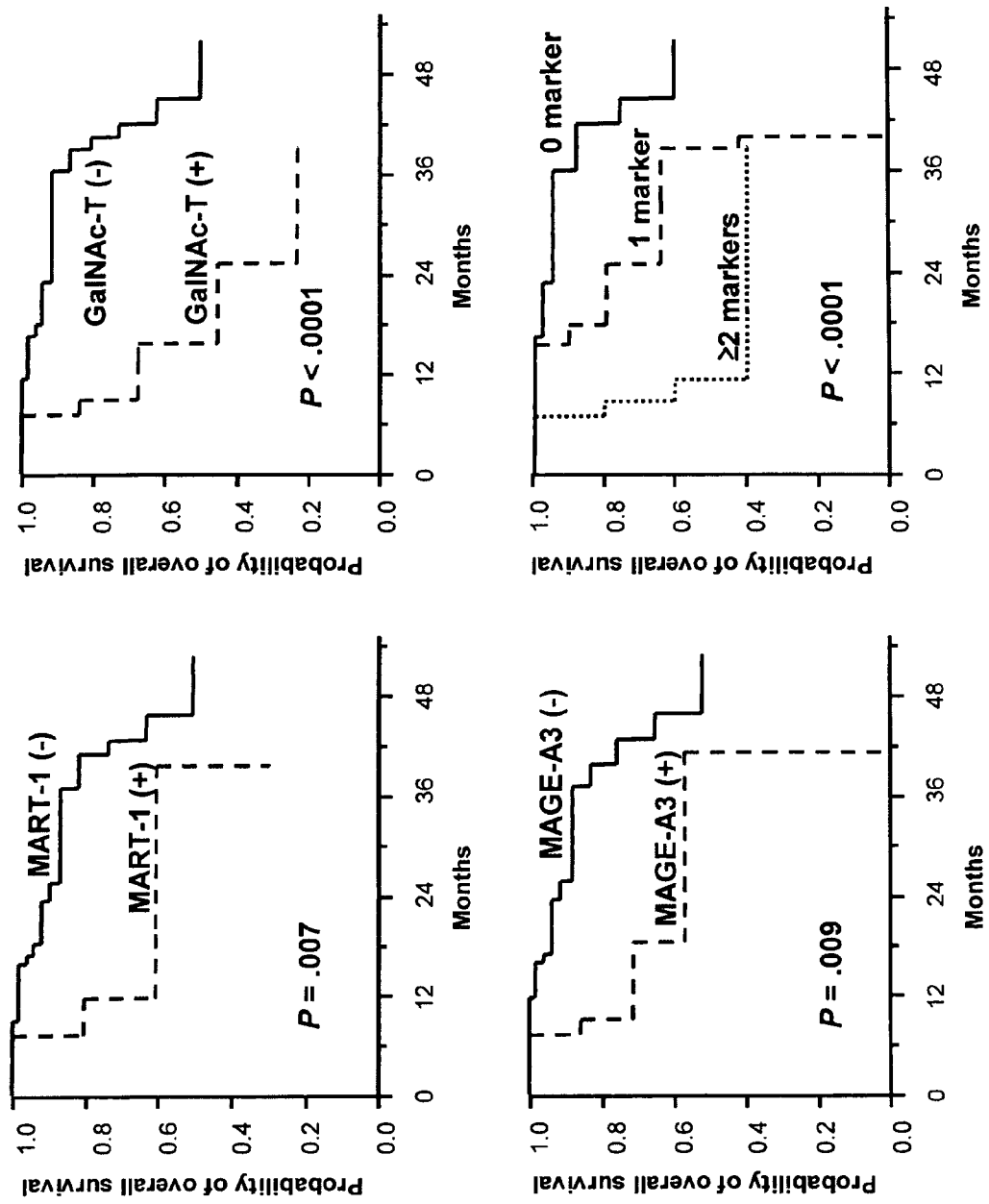
FIG. 5 shows Kaplan-Meier curves of overall survival (OS) based on marker detection after the treatment.

After treatment, OS decreased significantly if blood specimens were positive for MART-1, GalNAc-T, and/or MAGE-A3 (P=0.007, P<0.0001, and P=0.009, respectively) (FIG. 5). Again, the level of decrease was directly correlated with the number of positive markers (P<0.0001) (FIG. 5). For patients with no positive markers, no patients died within 12 months, and 4 patients died during follow-up period, and the estimated OS was 94.5±3.8% (estimate±SE) for 24 months. For patients with one positive marker, no patients died within 12 months, and 5 died, and the estimated OS was 80.0±12.7% for 24 months. For patients with >2 positive markers, 3 patients died within 12 months, and the estimated 1-year survival rate was 40.0±21.9%. Using a Cox proportional hazard regression model, number of positive markers after treatment (risk ratio=12.6; 95% CI, 3.16 to 50.5; P=0.0003) was selected as a significant independent prognostic factors for OS. No other factors were selected in Cox proportional model except age (>50 vs ≦50) (risk ratio=8.19; 95% CI, 2.30 to 28.5; P=0.001).

Discussion

Recent studies have shown the importance of CTCs in blood, however most have focused on correlation with staging and tumor burden (29, 32). We previously demonstrated the significance of CTCs for prediction of disease outcome in patients with AJCC stage III melanoma receiving melanoma vaccine (27, 28). Because CTCs may indicate systemic subclinical disease, their quantitative real-time detection can represent a surrogate marker for predicting outcome to adjuvant therapy. In this study, we demonstrated that multimarker qRT assay could detect CTCs in blood of AJCC stage III melanoma patients receiving BC before and after surgery and changes in multimarker detection were correlated with disease progression and overall survival.

The four mRNA markers selected for this study are frequently found in blood specimens from melanoma patients but not in blood from healthy individuals (31). Because metastatic melanoma tumors are heterogenous in melanoma-associated marker expression (9, 17), a combination of markers can compensate for variations in individual marker expression; thus we expect detection of tumor cells to be greatly increased and false-negative results reduced. Detection rates were higher with the multimarker qRT assay than with any individual marker assay. These findings indicate that a single-marker assay in blood has limited clinical utility (17, 25, 26).

The number of positive markers in each blood specimen significantly decreased across all three sampling intervals and during preoperative and postoperative BC. The nonsignificant decrease after surgery probably reflects residual tumor burden. CTCs were detected in more than half of patients after surgery, consistent with the high incidence of disease relapse in AJCC stage III melanoma patients. These findings also indicate the need for postoperative monitoring to detect systemic subclinical disease in patients who have undergone complete resection of stage III melanoma (33).

The change in marker detection rates was clearly different between relapse-free and relapse patients. Preoperative and postoperative BC significantly reduced the number of markers only in relapse-free patients. Marker detection after treatment also correlated with overall survival. These results suggest that serial monitoring of CTCs might be used to predict disease outcome. The fact that surgery did not significantly affect marker detection rates in both relapse-free or relapse patients suggests that subclinical systemic disease had already been established before operative intervention. Cox proportional model did not select the histopathological factor (pT and/or pN stage) as a prognostic factor, and these findings might indicate that assessment of primary and regional lymph node according to TNM staging criteria could not accurately predict the disease relapse and overall survival in patients receiving neoadjuvant treatment, because of modification of tumor burden by chemotherapeutic and/or immunotherapeutic drugs.

From a clinical standpoint, the development of a tool to identify high-risk patients and to monitor the response to adjuvant therapy in patients that are clinically disease-free would represent significant progress in the management of melanoma patients. Although most studies of CTCs in melanoma have used specimens obtained at only one time point, serial assessment can detect CTC changes during different phases of treatment. This makes CTC assessment a promising method to detect real-time subclinical tumor spreading. Although we did not measure clinical response to treatment, our assay system may have the potential to identify which component of treatment is most effective and which needs to be improved. As treatment regimens become multi-modal and multi-phasic, there will be an urgent need for clinically relevant surrogate markers that can be used to monitor response as well as predict outcome.

Most studies for assessment of predictive markers in patients treated with neoadjuvant therapy have used tumor tissues. However, static assessment of primary and metastatic tumor specimens after neoadjuvant therapy does not indicate whether tumor cells are being shed or whether treatment is reducing metastasis. In contrast, dynamic assessment of serially obtained blood specimens allows molecular evaluation of tumor cell shedding during treatment and is highly important to evaluate efficacy in controlling systemic disease. This study supports the use of molecular markers as surrogates for disease progression and suggests that our assay system could minimize sample variation from different sites and thereby increase the feasibility of multicenter studies.

REFERENCES

1. Greene et al., AJCC cancer staging manual, 6th ed., New York: Springer-Verlag, 2002.
2. Balch et al., J. Clin. Oncol. 19:3635-48, 2001.
3. Balch et al., Semin. Surg. Oncol. 21:43-52, 2003.
4. Kawakami et al., Proc. Natl. Acad. Sci. USA, 91:3515-9, 1994.
5. Marincola et al., Adv. Immunol. 74:181-273, 2000.
6. Schultz et al., Cancer Res. 60:6272-5, 2000.
7. Sarantou et al., Cancer Res., 57:1371-6, 1997.
8. Miyashiro et al., Clin. Chem. 47:505-12, 2001.
9. Takeuchi et al., J. Clin. Oncol. 22:2671-80, 2004.
10. Goding, Genes Dev. 14:1712-28, 2000.
11. Scholl et al., Cancer Res. 61:823-6, 2001.
12. Choi and Kusewitt, Vet. Pathol. 40:713-8, 2003.
13. Wascher et al., Clinical Cancer Research 9:1427-35, 2003.
14. Bouras et al., Cancer Research 62:1289-95, 2002.
15. Zehentner et al., Clinical Chemistry 50:2069-76, 2004.
16. Weitz et al., Clinical Cancer Research 7:3423-9, 2001.
17. Hoon et al., J. Clin. Oncol. 13:2109-16, 1995.
18. Innis et al., PCR Protocols, Academic Press, Inc., San Diego, Calif., 1990.
19. Bustin, Journal of Molecular Endocrinology 25:169-93, 2000.
20. Bostick et al., J. Clin. Oncol. 16:2632-40, 1998.
21. Takeuchi et al., Cancer Res. 63:441-8, 2003.
22. Irieet al., Lancet 1:786-7, 1989.
23. Gaugler et al., J. Exp. Med. 179:921-30, 1994.
24. Kawakami et al., J. Exp. Med. 180:347-52, 1994.
25. Glaser et al., J. Clin. Oncol. 15:2818-25, 1997.
26. Jung et al., J. Clin. Oncol. 15:2826-31, 1997.
27. Hoon et al., Cancer Res. 60:2253-7, 2000.
28. Wascher et al., J. Clin. Oncol. 21:2558-63, 2003.
29. Pantel et al., J. Natl. Cancer Inst. 91:1113-24, 1999.
30. Stathopoulou et al., Clin. Cancer Res. 9:5145-51, 2003.
31. Koyanagi et al., Clin. Chem. 51:981-8, 2005.
32. Cristofanilli et al., N. Engl. J. Med. 351:781-91, 2004.
33. Voit et al., J. Clin. Oncol. 23:1218-1227, 2005.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims. All literatures cited herein are incorporated by reference in their entirety.

What is claimed is:

1. A method of predicting melanoma recurrence in a subject and relapse-free survival of a subject, comprising:
   obtaining a body fluid from a first subject; and
   detecting the expression of a panel of genes in the body fluid, the panel of genes including PAX-3, GalNac-T, MAGE-A3, and MART-1,
   wherein, as compared to the number of the expressed genes selected from the group consisting of PAX-3, GalNac-T, MAGE-A3, and MART-1 in a body fluid obtained from a second subject, a higher number of the expressed genes selected from the group consisting of PAX-3, GalNac-T, MAGE-A3, and MART-1 in the body fluid obtained from the first subject indicates that the first subject has a higher probability of melanoma recurrence, and
   wherein, as compared to the expression of one or no gene selected from the group consisting of PAX-3, GalNac-T, MAGE-A3, and MART-1 in a body fluid obtained from a second subject, the expression of at least two genes selected from the group consisting of PAX-3, GalNac-T, MAGE-A3, and MART-1 in the body fluid obtained from the first subject indicates that the first subject has a likelihood of a shorter relapse-free survival.

2. The method of claim 1 wherein at least one gene selected from the group consisting of GalNAc-T; MAGE-A3, MART-1, and PAX-3 is expressed in the body fluid obtained from the first subject.

3. The method of claim 1, wherein the body fluid is blood, bone marrow, cerebral spinal fluid, lymph fluid, peritoneal fluid, or pleural fluid.

4. The method of claim 1, wherein at least two genes selected from the group consisting of GalNAc-T, MAGE-A3, MART-1, and PAX-3 are expressed in the body fluid obtained from the first subject.

5. The method of claim 4, wherein at least three genes selected from the group consisting of GalNAc-T, MAGE-A3, MART-1, and PAX-3 are expressed in the body fluid obtained from the first subject.

6. The method of claim 5, wherein at least four genes selected from the group consisting of GalNAc-T, MAGE-A3, MART-1, and PAX-3 are expressed in the body fluid obtained from the first subject.

7. The method of claim 1, wherein the subject is suffering from a subclinical or clinical systemic melanoma.

8. The method of claim 1, wherein the melanoma recurrence is predicted for a period of at least three years following the removal of a primary tumor, SLND, or both.

9. The method of claim 1, wherein the body fluid sample from the subject is histopathologically negative for melanoma cells.

10. The method of claim 9, wherein the histopathology of the body fluid sample is determined by H&E or IHC staining.

* * * * *

```
                            SEQUENCE LISTING

<160> NUMBER OF SEQ ID NOS: 5

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
tgcagaacag tcaccaccac c                                               21

<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 2
atgaggctgc tttcactatc cgca                                            24

<210> SEQ ID NO 3
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 3
ccagactgat tacgcgctct ccc                                             23

<210> SEQ ID NO 4
```

```
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 4
agctcctgcc cacactcccg cctgt                                              25

<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 5
cagcaatgcc tcctgcacca ccaa                                               24
```